US009776986B2

(12) United States Patent
Meng et al.

(10) Patent No.: US 9,776,986 B2
(45) Date of Patent: Oct. 3, 2017

(54) PARASITICIDAL COMPOSITIONS COMPRISING INDOLE DERIVATIVES, METHODS AND USES THEREOF

(71) Applicant: MERIAL, INC., Duluth, GA (US)

(72) Inventors: Charles Meng, Grayson, GA (US); Loïc Le Hir de Fallois, Atlanta, GA (US)

(73) Assignee: MERIAL INC., Duluth, GA (US)

( * ) Notice: Subject to any disclaimer, the term of this patent is extended or adjusted under 35 U.S.C. 154(b) by 0 days.

(21) Appl. No.: 14/744,166

(22) Filed: Jun. 19, 2015

(65) Prior Publication Data

US 2015/0366198 A1    Dec. 24, 2015

Related U.S. Application Data

(60) Provisional application No. 62/014,245, filed on Jun. 19, 2014.

(51) Int. Cl.
| | |
|---|---|
| *C07D 209/08* | (2006.01) |
| *C07D 401/12* | (2006.01) |
| *C07D 209/10* | (2006.01) |
| *C07D 401/04* | (2006.01) |
| *H03K 5/04* | (2006.01) |
| *H03K 7/00* | (2006.01) |

(52) U.S. Cl.
CPC ......... *C07D 401/12* (2013.01); *C07D 209/08* (2013.01); *C07D 209/10* (2013.01); *C07D 401/04* (2013.01); *H03K 5/04* (2013.01); *H03K 7/00* (2013.01)

(58) Field of Classification Search
CPC ............................ C07D 209/08; C07D 401/04
See application file for complete search history.

(56) References Cited

FOREIGN PATENT DOCUMENTS

| | | |
|---|---|---|
| WO | WO 2011/060746 A1 | 5/2011 |
| WO | WO 2012/088431 A1 | 6/2012 |

OTHER PUBLICATIONS

Spycher, et al. Document No. 150:532288, retrieved from CAPLUS; (2008).*
Poletto et al., "Synthesis and anti-inflammatory evaluation of certain 5-alkoxy-2,7-dialkyltryptamines," Journal of Medicinal Chemistry, vol. 16, No. 7; Jul. 1, 1973, pp. 757-765, compounds VIa, VIb, XIVa, XIVb, XVa, XVb. XP055208658; ISSN 0022-2623.
Conde J J et al., "Towards the synthesis of osteoclast inhibitor SB-242784," Tetrahedron Letters, Pergamon, GB, vol. 44, No. 15, Apr. 7, 2003; pp. 3081-3084, compounds 4, 14; XP004415666; ISSN 0040-4039.
Wang et al., "Fluorinated N-[2-(haloalkyl)phenyl]imidoyl chloride, a key intermediate for the synthesis of 2-fluoroalkyl substituted indole derivatives via Grignard cyclization process," Journal of Fluorine Chemistry, Elsevier, NL, vol. 128, No. 18, Oct. 1, 2007; pp. 1143-1152; compounds 5c, 5h, 5j; XP022278619, ISSN 0022-1139.
Hong X et al., "Photodesulfonylation of indoles initiated by electron transfer from trimethylamine," Tetrahedron Letters, Pergamon, GB, vol. 47, No. 14, Apr. 3, 2006; pp. 2409-2412, compound 15b, XP025003850, ISSN 0040-4039.
Can Zhu et al., "Coupling and cyclization of O-Iodoanilines and propargylic bromides via allenes: an efficient entry to indomethacin," Organic Letters, vol. 15 No. 11, Jun. 7, 2013; pp. 2782-2785, compound 8p, XP055208669, ISSN 1523-7060.
Politanskaya et al., "Synthesis of indoles with a polyfluorinated benzene ring," Tetrahedron, vol. 69, No. 39, Jul. 17, 2013, pp. 8477-8486, compounds 2ba, 2ca, XP 055208661, ISSN 0040-4020.
Hernandez-Luis et al., "Synthesis and biological activity of 2-(trifluoromethyl)-1-benzimidazole derivatives against some protozoa and *Trichinella spiralis*," European Journal of Medicinal Chemistry, Editions Scientifique, Elsevier, Paris FR, vol. 45, No. 7, Mar. 31, 2010; pp. 3135-3141, compounds 1a, 1d, 1e, 1h, 1i, XP028303009, ISSN 0223-5234.

* cited by examiner

*Primary Examiner* — Shawquia Jackson
(74) *Attorney, Agent, or Firm* — Judy Jarecki-Black; Katrina Bergbauer; Merial Inc.

(57) ABSTRACT

The invention relates to oral, topical or injectable compositions for combating liver fluke parasites in mammals, comprising at least one indole derivative active agent. The invention also provides for an improved method for eradicating and controlling liver fluke parasite infections and infestations in a mammal comprising administering the compositions of the invention to the mammal in need thereof.

27 Claims, 1 Drawing Sheet

PARASITICIDAL COMPOSITIONS COMPRISING INDOLE DERIVATIVES, METHODS AND USES THEREOF

INCORPORATION BY REFERENCE

This application claims priority to provisional application U.S. Ser. No. 62/014,245, filed on 19 Jun. 2014, and incorporated by reference herein in its entirety.

FIELD OF THE INVENTION

The present invention provides parasiticidal indole derivatives and oral, topical or injectable veterinary compositions comprising an indole derivative active agent for controlling liver flukes in mammals. The use of these compounds and compositions against liver flukes and methods for treating parasitic infections and infestations in mammals is presented herein.

BACKGROUND OF THE INVENTION

Animals such as mammals (including humans) are often susceptible to parasite infections and infestations. These parasites may be ectoparasites, such as insects, and endoparasites such as filariae and other worms. Production animals, such as cows, pigs, sheep and goats, can be infected with one or more trematodes. Of particular concern here is *Fasciola hepatica* (i.e., liver fluke or *F. hepatica*).

Liver flukes are a particular problem because they adversely affect the health of the animal or human and can inflict significant economic loss in a domestic livestock population. It is estimated that *F. hepatica* poses a risk to at least 250 million sheep and 350 million cattle worldwide. Moreover, domestic animals other than sheep and cows may serve as intermediate hosts. Liver flukes can cause liver condemnation, secondary infections, reduced milk and meat production, abortion and fertility problems.

Several types of control measures for liver flukes have been introduced over the past century. First, halogenated hydrocarbons (e.g., $CCl_4$; carbon tetrachloride) were introduced for ruminants in the 1920s. Halogenated hydrocarbons had limited success and are no longer used primarily because of their adverse effects and variable efficacy. Second, halogenated phenols were administered in the late 1950s (e.g., hexachlorophene and bithionol sulfoxide) followed by the similar halogenated salicylanilides (e.g., oxyclozanide, bromoxanide). Fourth, benzimidazole carbamates (e.g., albendazole, luxabendazole) were found to have a broad anthelmintic spectrum against nematodes and mature *F. hepatica*. Another benzimidazole—the chlorinated methylthiobenzimidazole derivative triclabendazole—has a high success rate against *F. hepatica*. Fifth, bisanilino compounds introduced in the 1960s were intolerable due to toxic side effects. Finally, benzene sulfonamides (e.g., clorsulon) were studied in the 1970s. Extensively modified examples of this class demonstrate high efficacy on both mature and immature *F. hepatica*. Of these six classes of anthelmintics the benzimidazole class is perhaps the most widely used for its high efficacy.

Indeed, triclabendazole is the current drug of choice against mature and immature liver flukes. Not surprisingly, however, reports of parasite resistance are increasing. For example, Mottier et al., report that a population of resistant *F. hepatica* (Sligo) may use an altered influx/efflux mechanism to selectively decrease the amount of triclabendazole and triclabendazole sulfoxide but not albendazole. See Mottier et al., *J. Parasitol.*, 92(6), 2006, pp. 1355-1360. McConville et al., report that juvenile triclabendazole-resistant *F. hepatica* are somewhat susceptible to compound alpha (i.e., 5-chloro-2-methylthio-6-(1-naphthyloxy)-1H-benzimidazole) via a tubulin-independent mechanism. See McConville et al., Parasitol. Res., (2007) 100:365-377. Further, Keiser et al., report the testing of artemether and OZ78 in triclabendazole-resistant *F. hepatica*, although at high concentrations. For a short review of triclabendazole resistance see Brennan et al., Experimental and Molecular Pathology, 82, (2007) pp. 104-109.

There is, however, little in the literature disclosing indoles as a treatment for trematodes. Derquantel is in a class known as spiroindoles and is paired with a macrocyclic lactone for greater efficacy against sheep nematodes (e.g., gastrointestinal and respiratory parasites) but no data is currently available as to the effectiveness of derquantel against trematodes.

Other indole compounds have demonstrated an effect on *F. hepatica*. Indolamines such as serotonin (5-hydroxytryptamine) have a stimulant effect on the rhythmical activity of the trematode that is antagonized by other compounds also having an indole structure (e.g., bromolysergic acid diethylamide and yohimbine; Mansour, *Brit. J. Pharmacol.* (1957), 12, 406.)

WO 2007/051619 discloses aryl indole derivatives as pesticides. The '619 application speculates that the aryl indole derivatives that it discloses would be effective against trematodes such as *F. hepatica* but offers evidence only against the dog tick, the cat flea, and certain gastrointestinal nematodes.

WO 2012/125662 discloses indole derivatives useful as ccr2 (i.e., chemokine receptor type 2) antagonists. The '662 application further speculates that the compounds of its disclosure may be effective against trematodes but offers no evidence of such.

Similarly, WO 2012/059232 discloses carbazole and carboline derivatives, and preparation and therapeutic applications thereof. The compounds reportedly are useful against proliferative diseases and parasitic diseases. The authors present evidence that some compounds disclosed inhibit tubulin polymerization for possible application against proliferative diseases but no evidence is presented for activity against trematodes.

The resistance to triclabendazole and lack of effective substitutes creates a pressing need in the field for alternatives that exhibit low side effects and that do not contaminate the animals as a food source. Optimal compositions should further be efficacious, have a quick onset of activity, have a long duration of activity, and be safe to the animal recipients and their human owners.

INCORPORATION BY REFERENCE

Any abovementioned applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

SUMMARY OF THE INVENTION

The present invention is directed to compounds and compositions for treating helminth infestation comprising an anthelmintically effective amount of indole compounds of formula (I) described herein and their use to control parasites in mammals to include humans. In accordance with this invention, it has been discovered that these compounds show unexpected efficacy and speed of onset.

The invention encompasses uses or veterinary uses of the oral, topical or injectable indole compositions comprising an anthelmintically effective amount of indole compounds of formula (I) for the treatment or prophylaxis of parasitic trematode infections and infestations of animals (either wild or domesticated), including livestock and companion animals such as cats, dogs, horses, sheep, goats, pigs and cattle, with the aim of ridding these hosts of liver flukes encountered by such animals. The composition may also be suitable for humans.

The invention also provides methods for treating helminth infestation comprising administration of an anthelmintically effective amount of the compound(s) of formula (I) to an animal in need thereof. Surprisingly, it has been found that the inventive compositions and formulations described herein exhibit superior efficacy against *F. hepatica* compared to compositions known in the art.

The invention does not intentionally seek to encompass any previously known product, process of making the product, or method of using the product such that the Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product. The invention and its embodiments are disclosed by the following Detailed Description.

DETAILED DESCRIPTION

Figure 1A:
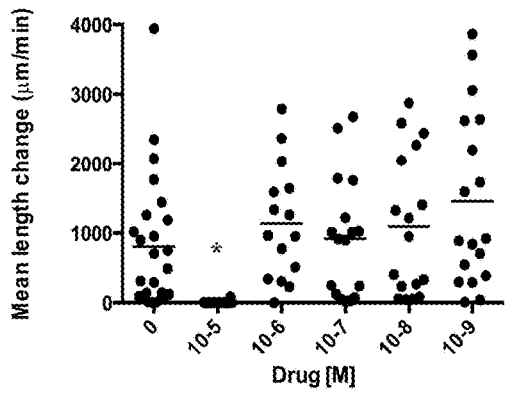
FIG. 1A shows the effect of various triclabendazole concentrations on liver fluke motility.

In this disclosure and in the claims, terms such as "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

It is also noted that in this disclosure and in the claims and/or paragraphs, the compounds of the invention are intended to include all stereoisomers and crystalline forms (which includes hydrated forms, polymorphic forms and amorphous forms with up to 15% by weight crystalline structure) thereof.

DEFINITIONS

Terms used herein will have their customary meaning in the art unless specified otherwise. The organic moieties mentioned in the definitions of the variables of formula (I) are—like the term halogen—collective terms for individual listings of the individual group members. The prefix $C_n$-$C_m$ indicates in each case the possible number of carbon atoms in the group.

The term "animal" is used herein to include all mammals and also include all vertebrate animals. Animals include, but are not limited to, cats, dogs, cattle, cows, deer, goats, horses, llamas, pigs, sheep and yaks. It also includes an individual animal in all stages of development, including embryonic and fetal stages. In some embodiments, the animal may be a human animal.

The term "alkyl" refers to saturated straight, branched, cyclic, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups or "cycloalkyl", which are encompassed by alkyl include those with 3 to 10 carbon atoms having single or multiple condensed rings. In some embodiments, cycloalkyl groups include $C_4$-$C_7$ or $C_3$-$C_4$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

The alkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamoyl, ester, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

Terms including the term "alkyl" such as "alkylcycloalkyl," "cycloalkylalkyl," "alkylamino," or "dialkylamino" will be understood to comprise an alkyl group as defined above linked to the other functional group, where the group is linked to the compound through the last group listed, as understood by those of skill in the art.

The term "alkenyl" refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkynyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "alkylthio" refers to alkyl-S—, wherein alkyl is as defined above. Similarly, the terms "haloalkylthio," "cycloalkylthio," and the like, refer to haloalkyl-S— and cycloalkyl-S— where haloalkyl and cycloalkyl are as defined above.

The term "alkylsulfinyl" refers to alkyl-S(O)—, wherein alkyl is as defined above. Similarly, the term "haloalkylsulfinyl" refers to haloalkyl-S(O)— where haloalkyl is as defined above.

The term "alkylsulfonyl" refers to alkyl-S(O)$_2$—, wherein alkyl is as defined above. Similarly, the term "haloalkylsulfonyl" refers to haloalkyl-S(O)$_2$— where haloalkyl is as defined above.

The term alkylamino and dialkylamino refer to alkyl-NH— and (alkyl)$_2$N— where alkyl is as defined above. Similarly, the terms "haloalkylamino" refers to haloalkyl-NH— where haloalkyl is as defined above.

The terms "alkylcarbonyl," "alkoxycarbonyl," "alkylaminocarbonyl," and "dialkylaminocarbonyl refer to alkyl-C(O)—, alkoxy-C(O)—, alkylamino-C(O)— and dialkylamino-C(O)— where alkyl, alkoxy, alkylamino and dialkylamino are as defined above. Similarly, the terms "haloalkylcarbonyl," "haloalkoxycarbonyl,"

"haloalkylaminocarbonyl," and "dihaloalkylaminocarbonyl" refer to the groups haloalkyl-C(O)—, haloalkoxy-C(O)—, haloalkylamino-C(O)— and dihaloalkylamino-C(O)— where haloalkyl, haloalkoxy, haloalkylamino and dihaloalkylamino are as defined above.

"Aryl" refers to a monovalent aromatic carbocyclic group of from 6 to 14 carbon atoms having a single ring or multiple condensed rings. In some embodiments, aryl groups include $C_6$-$C_{10}$ aryl groups. Aryl groups include, but are not limited to, phenyl, biphenyl, naphthyl, tetrahydronaphthyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl)amino, or trialkylsilyl. Aryl groups may be linked to other moieties via an ether linkage.

The term "aralkyl" refers to an aryl group that is bonded to the parent compound through a diradical alkylene bridge, (—$CH_2$—)—, where n is 1-12 and where "aryl" is as defined above.

"Heteroaryl" refers to a monovalent aromatic group of from 1 to 15 carbon atoms, such as from 1 to 10 carbon atoms, having one or more oxygen, nitrogen, and sulfur heteroatoms within the ring, for example 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple condensed rings provided that the point of attachment is through a heteroaryl ring atom. Heteroaryls may include pyridyl, pyridazinyl, pyrimidinyl, pyrazinyl, triazinyl, pyrrolyl, indolyl, quinolinyl, isoquinolinyl, quinazolinyl, quinoxalinyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings may be unsubstituted or substituted by one or more moieties as described for aryl above. Heteroaryl groups may be linked to other moieties via an ether linkage.

"Heterocyclyl," "heterocyclic" or "heterocyclo" refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, which have one or more oxygen, sulfur or nitrogen heteroatoms in ring, such as 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl]or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl, and the like.

Halogen means the atoms fluorine, chlorine, bromine and iodine. The designation of "halo" (e.g., as illustrated in the term haloalkyl) refers to all degrees of substitutions from a single substitution to a perhalo substitution (e.g., as illustrated with methyl as chloromethyl (—$CH_2Cl$), dichloromethyl (—$CHCl_2$), trichloromethyl (—$CCl_3$)).

Stereoisomers and Polymorphic Forms

It will be appreciated by those of skill in the art that certain compounds within the compositions of the invention may exist and be isolated as optically active and racemic forms. Compounds having one or more chiral centers, including at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds within the compositions of the invention may include one or more chiral centers, which results in a theoretical number of optically active isomers. Where compounds within the compositions of the invention include "n" chiral centers, the compounds may comprise up to $2^n$ optical isomers. The present invention encompasses the specific enantiomers or diastereomers of each compound as well as mixtures of different enantiomers and/or diastereomers of the compounds of the invention that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds within the compositions of the present invention may also be present in different solid forms such as different crystalline forms or in the form of an amorphous solid. The present invention encompasses different crystalline forms as well as amorphous forms of the inventive compounds.

In addition, the compounds within the compositions of the invention may exist as hydrates or solvates, in which a certain stoichiometric amount of water or a solvent is associated with the molecule in the crystalline form. The compositions of the invention may include hydrates and solvates of the active agents.

Salts

Also contemplated within the scope of the invention are acid or base salts, where applicable, of the compounds of the invention provided for herein.

The term "acid" contemplates all pharmaceutically acceptable inorganic or organic acids. Inorganic acids include mineral acids such as hydrohalic acids such as hydrobromic acid and hydrochloric acid, sulfuric acid, phosphoric acids and nitric acid. Organic acids include all pharmaceutically acceptable aliphatic, alicyclic and aromatic carboxylic acids, dicarboxylic acids, tricarboxylic acids and fatty acids. In one embodiment of the acids, the acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, acetic acid, propionic acid, isopropionic acid, valeric acid, α-hydroxy acids such as glycolic acid and lactic acid, chloroacetic acid, benzoic acid, methane sulfonic acid, and salicylic acid. Examples of dicarboxylic acids include oxalic acid, malic acid, succinic acid, tartaric acid, fumaric acid, and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylstearic acid. Other acids include gluconic acid, glycoheptonic acid and lactobionic acid.

The term "base" contemplates all pharmaceutically acceptable inorganic or organic bases, including hydroxides, carbonates or bicarbonates of alkali metal or alkaline earth metals. Salts formed with such bases include, for example, the alkali metal and alkaline earth metal salts, including, but not limited to, as the lithium, sodium, potassium, magnesium or calcium salts. Salts formed with organic bases include the common hydrocarbon and heterocyclic amine salts, which include, for example, ammonium salts ($NH_4^+$), alkyl- and dialkylammonium salts, and salts of cyclic amines such as the morpholine and piperidine salts.

The term "derivative" contemplates a compound obtained from or closely related to another substance or compound. A derivative contemplates a chemical compound that may be produced from another chemical compound of similar structure in one or more steps.

In one embodiment, the invention provides novel oral, topical or injectable veterinary compounds according to formula (I) below.

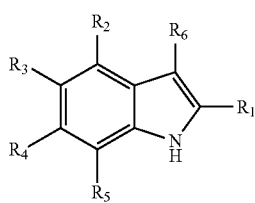

(I)

wherein:
R$_1$ is ($C_1$-$C_6$)-alkyl, ($C_2$-$C_5$)-alkenyl, or ($C_2$-$C_5$)-alkynyl, each independently unsubstituted or substituted with one or more halogens; R$_2$ is H, halogen, ($C_1$-$C_6$)-alkyl or ($C_1$-$C_6$) haloalkyl; R$_3$ is halogen, ($C_1$-$C_6$)-alkyl, ($C_2$-$C_5$)-alkenyl, or ($C_2$-$C_5$)-alkynyl, ($C_1$-$C_6$)-alkoxy, thienyl, furanyl, biphenyl, naphthyl, tetralin ether, aryl, aryl ether, sulfonylaryl, sulfoxyaryl, thioaryl, ($C_3$-$C_6$)-cycloalkyl, or pyridinyl, wherein the last seven substituents may be unsubstituted or substituted with one or more of halogen, ($C_1$-$C_3$)-haloalkyl, ($C_1$-$C_3$)-haloalkoxy or carboxyl; R$_4$ is H, halogen, ($C_1$-$C_6$)-alkyl or ($C_1$-$C_6$)-haloalkyl; R$_5$ is H, halogen, ($C_1$-$C_6$)-alkyl or ($C_1$-$C_6$)-haloalkyl; and R$_6$ is H, halogen, ($C_1$-$C_6$)-alkyl, ($C_2$-$C_5$)-alkenyl, or ($C_2$-$C_5$)-alkynyl, wherein each of ($C_1$-$C_6$)-alkyl, ($C_2$-$C_5$)-alkenyl, or ($C_2$-$C_5$)-alkynyl is independently unsubstituted or substituted with one or more halogens.

In another embodiment, the compound of formula (I) defines R$_1$ as ($C_1$-$C_4$)-alkyl substituted with fluorine. In yet another embodiment, the compound of formula (I) defines R$_2$ as chlorine.

In another embodiment, the compound of formula (I) defines R$_3$ as a mono- or di-halo substituted phenyl ether. In another embodiment, the compound of formula (I) defines R$_3$ as a di- or tri-halo substituted phenyl. In yet another embodiment, the compound of formula (I) defines R$_3$ as chlorine, bromine or fluorine.

In another embodiment, the compound of formula (I) defines R$_4$ as chlorine. In another embodiment, the compound of formula (I) defines R$_5$ as hydrogen.

In another embodiment, the compound of formula (I) is 5-[2-chloro-4-(trifluoromethyl)phenyl]-2-(trifluoromethyl)-1H-indole. In another embodiment, the compound of formula (I) is 6-[2-chloro-4-(trifluoromethyl)phenyl]-2-(trifluoromethyl)-1H-indole. In another embodiment, the compound of formula (I) is 6-chloro-5-[2-chloro-4-(trifluoromethyl)phenyl]-2-(trifluoromethyl)-1H-indole. In another embodiment, the compound of formula (I) is 6-chloro-2-(trifluoromethyl)-5-[4-(trifluoromethyl)phenyl]-1H-indole.

In another embodiment, the compound of formula (I) is 6-chloro-5-(2-chlorophenyl)-2-(trifluoromethyl)-1H-indole.

In another aspect, the invention is a composition for treating helminth infestation comprising an anthelmintically effective amount of the compounds of formula (I) defined above and a pharmaceutically acceptable carrier.

In another embodiment, the composition including formula (I) is combined with a macrocyclic lactone. In one embodiment, the macrocyclic lactone is an avermectin. In another embodiment, the macrocyclic lactone is ivermectin.

In yet another embodiment, the composition including formula (I) is combined with verapamil. Verapamil and macrocyclic lactones such as avermectins may provide a synergistic effect in combination with compounds of formula (I) to kill triclabendazole-resistant liver flukes.

The synergistic effect is thought to occur due to the inhibition of the P-glycoprotein drug transporter by verapamil or the avermectin.

In another aspect, the invention is a method for treating helminth infestation comprising administration of an anthelmintically effective amount of the compounds defined above to an animal in need thereof. The helminths are, for example, trematodes, and may be specifically F. hepatica.

Experimental Procedure and Results

Representative compounds of formula (I) were tested in vitro against F. hepatica as follows. Adult F. hepatica (fluke) were collected from infected bovine livers obtained from a local abattoir (Basel, Switzerland). The worms were quickly washed with 0.9% (w/v) NaCl and placed in 6 or 12-well plates (Costar). Culture medium in each well contained RPMI 1640 (Gibco) at 37° C., which was supplemented with antibiotics (50 µg/ml streptomycin and 50 IU/ml penicillin; Gibco) and 80 µg/ml of a haemin solution. The haemin solution was prepared as follows: 5 mg haemin was dissolved in 1 ml of 0.1M aqueous solution of NaOH, and 3.95 ml of PBS (pH=7.4) and 0.05 ml of 1M HCl were added to adjust the pH to 7.1-7.4 (Keiser and Morson, 2008). Cultures were kept at 37° C. in an atmosphere of 5% $CO_2$. To monitor the temporal effects of test compounds in vitro, 3 flukes were incubated for 72 h in the presence of 50 or 100 µg/ml of each test compound. At 24, 48, and 72 h, worms were examined using a dissecting microscope. For the adult worms, a viability scale ranging from 3 (normal movements) to 0 (death; no movement observed for two min using a microscope) was used. Test compounds that showed activity at a concentration of 50 μg/ml were further evaluated at lower concentrations (20 μg/ml, 10 μg/ml, 5 μg/ml, 2.5 μg/ml, 1.25 μg/ml and 0.625 μg/ml).

Table 1 lists representative compounds of formula (I) of the present invention and their effective in vitro concentrations against *F. hepatica*. All compounds were tested in vitro on the adult stage of *F. hepatica* as described above. Each data point refers to at least two independent experiments having at least three worms per concentration.

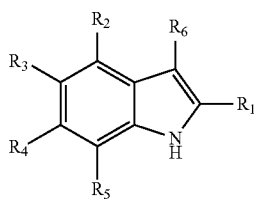

(I)

TABLE 1

| Compound No. | Structure | Effective in vitro concentration; μg/mL |
|---|---|---|
| 332 | F₃C—⌬—⌬—CF₃ (indole) | <10 |
| 334 | F₃C—⌬(Cl)—⌬—CF₃ (indole) | <10 |
| 336 | F₃C—⌬(Cl)—⌬(Cl)—CF₃ (indole) | <10 |
| 337 | F₃C—⌬(Cl)—⌬(Cl)—CH₃ (indole) | <10 |

TABLE 1-continued

| Compound No. | Structure | Effective in vitro concentration; μg/mL |
|---|---|---|
| 338 | F₃C—⌬(Cl)—⌬(Cl)—Et (indole) | <10 |
| 339 | F₃C—⌬(Cl)—⌬(Cl)—Pr (indole) | <10 |
| 340 | F₃C—⌬(Cl)—⌬(Cl)—CF₂CF₃ (indole) | <10 |
| 341 | F₃C—⌬(Cl)—⌬(Cl)—C₂F₄CF₃ (indole) | >10 |
| 342 | Cl—⌬(CF₃)—⌬(Cl)—CF₃ (indole) | <10 |
| 343 | Cl—⌬—⌬(Cl)—CF₃ (indole) | <10 |
| 344 | F—⌬—⌬(Cl)—CF₃ (indole) | <10 |
| 345 | F₃C—⌬—⌬(Cl)—CF₃ (indole) | <10 |

TABLE 1-continued

| Compound No. | Structure | Effective in vitro concentration; μg/mL |
|---|---|---|
| 346 | 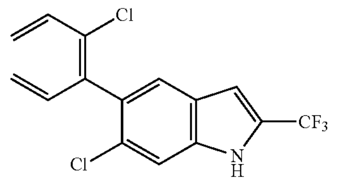 [SMILES: C=C/C(Cl)=C(\C=C)c1cc2cc(C(F)(F)F)[nH]c2cc1Cl] | <10 |
| 347 | 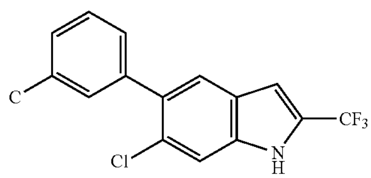 [SMILES: Cc1cccc(-c2cc3cc(C(F)(F)F)[nH]c3cc2Cl)c1] | ≤10 |
| 348 | 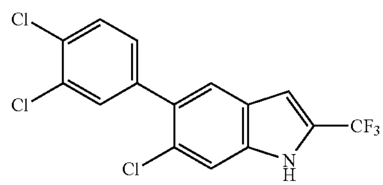 [SMILES: FC(F)(F)c1cc2cc(-c3ccc(Cl)c(Cl)c3)c(Cl)cc2[nH]1] | <10 |
| 349 | 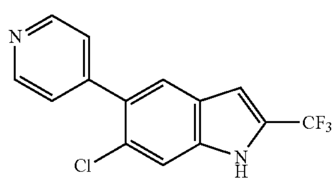 [SMILES: FC(F)(F)c1cc2cc(-c3ccncc3)c(Cl)cc2[nH]1] | ≤10 |
| 350 | 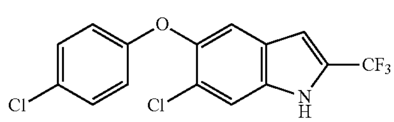 [SMILES: FC(F)(F)c1cc2cc(Oc3ccc(Cl)cc3)c(Cl)cc2[nH]1] | ≤10 |
| 351 | 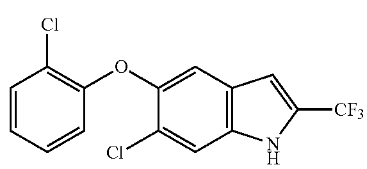 [SMILES: FC(F)(F)c1cc2cc(Oc3ccccc3Cl)c(Cl)cc2[nH]1] | <10 |
| 352 | 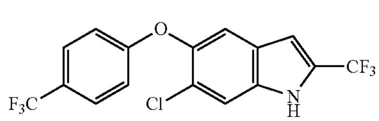 [SMILES: FC(F)(F)c1ccc(Oc2cc3cc(C(F)(F)F)[nH]c3cc2Cl)cc1] | >10 |
| 354 | 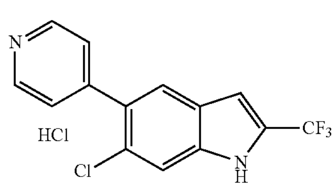 [SMILES: FC(F)(F)c1cc2cc(-c3ccncc3)c(Cl)cc2[nH]1 ; Cl] | >2.5 |
| 355 | 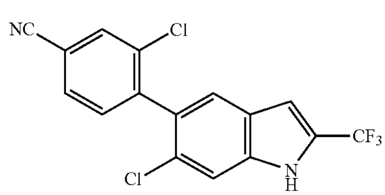 [SMILES: N#Cc1ccc(-c2cc3cc(C(F)(F)F)[nH]c3cc2Cl)c(Cl)c1] | ≥2.5 |
| 356 | | <10 |
| 357 | | <10 |
| 358 | | >2.5 |
| 359 | | >2.5 |
| 360 | | >2.5 |
| 360-0A | | >2.5 |
| 361 | | <10 |

TABLE 1-continued

| Compound No. | Structure | Effective in vitro concentration; µg/mL |
|---|---|---|
| 361-0A | 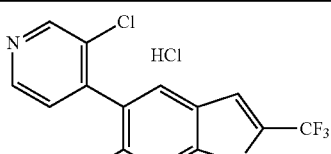 | <10 |
| 362 | 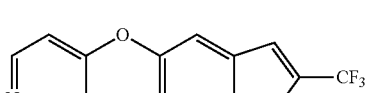 | >2.5 |
| 362-0A | 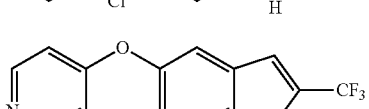 | >2.5 |

Figure 1B:
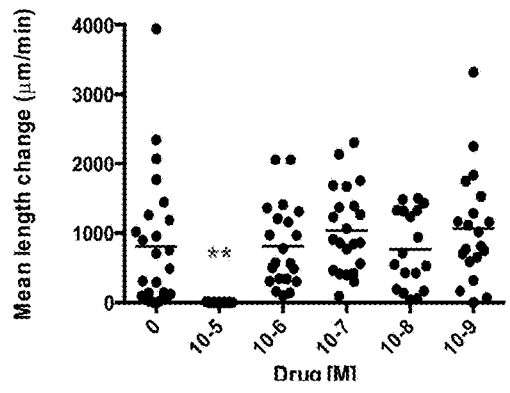
FIG. 1B shows the effect of various triclabendazole sulfoxide concentrations on liver fluke motility.
Figure 1C:
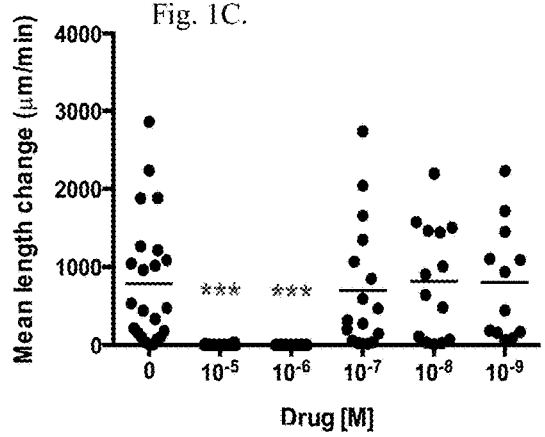
FIG. 1C shows the effect of various concentrations of compound 332 on liver fluke motility.
Figure 1D:
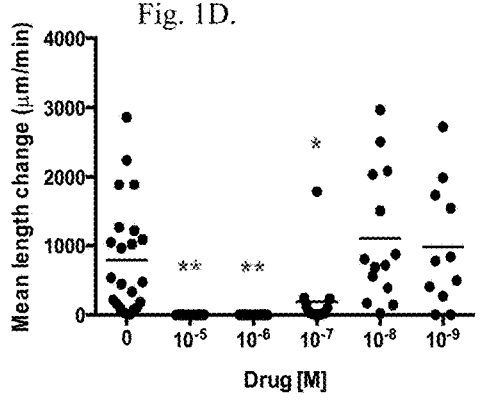
FIG. 1D shows the effect of various concentrations of compound 336 on liver fluke motility.
Figure 1E:
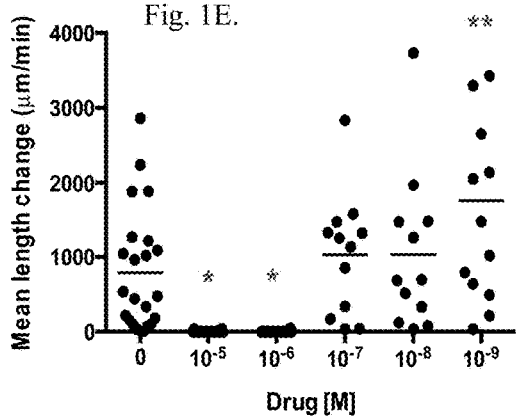
FIG. 1E shows the effect of various concentrations of compound 351 on liver fluke motility.

Further testing employed a fluke motility assay. Compounds 332, 336 and 351 were screened for activity against liver fluke newly-excysted juveniles (NEJs) in a digital image-based motility assay, based on measurement of the rate of change in worm length (µm/min) during peristaltic motility. Newly excised worms were immediately placed into a solution of drug in RPMI (final concentrations 10 µM-1 nM), alongside untreated and vehicle controls, and triclabendazole/triclabendazole sulfoxide (i.e., TCBZ/TCBZ-SO) at matching concentrations, for a period of 18 h. Each treatment group consisted of 15-20 NEJs. Compounds 332 (FIG. 1C), 336 (FIG. 1D) and 351 (FIG. 1E) showed more potent inhibition of motility than either TCBZ (FIG. 1A) or TCBZ-SO (FIG. 1B; both effective only at 10 µM). Compounds 332 and 351 completely abolished motility at 1 µM, while compound 336 significantly impacted motility at 100 nM. See FIG. 1. Each data point represents mean length change (µm/min) in an individual worm during a five minute recording period. Horizontal lines represent data set means. **, $p<0.0001$; *, $p<0.001$; **, $p<0.01$; *, $p<0.05$.

Additional veterinary/pharmaceutical active ingredients may be used with the compositions of the invention for oral, topical or injectable use. In some embodiments, the additional active agents may include, but are not limited to, acaricides, anthelmintics, anti-parasitics and insecticides. Anti-parasitic agents can include both ectoparasiticidal and endoparasiticidal agents.

Veterinary pharmaceutical agents that may be included in the compositions of the invention are well-known in the art (see e.g., *Plumb' Veterinary Drug Handbook*, 5th Edition, ed. Donald C. Plumb, Blackwell Publishing, (2005) or *The Merck Veterinary Manual*, 9th Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, chlorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/–clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (Oxyglobin®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, *propionibacterium acnes* injection, propofol, propranolol, protamine sulfate, pseudoephedrine, *psyllium* hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In another embodiment of the invention, one or more macrocyclic lactones or lactams, which act as an acaricide, anthelmintic agent and/or insecticide, can be added to the compositions of the invention.

The macrocyclic lactones include, but are not limited to, avermectins, such as abamectin, dimadectin, doramectin, emamectin, eprinomectin, ivermectin, latidectin, lepimectin, selamectin, ML-1,694,554 and milbemycins, such as milbemectin, milbemycin D, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" 12th ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054.

In another embodiment, the invention comprises a composition comprising an indole compound in combination with verapamil. Verapamil is believed to be an inhibitor of P-glycoprotein, which is a membrane protein that has been shown to efflux triclabendazole from triclabendazole-resistant *F. hepatica*. Inhibiting the efflux mechanism could allow the benzimidazole derivative to accumulate to toxic levels in the parasite.

In another embodiment, the invention comprises a composition comprising an indole compound in combination with a class of acaricides or insecticides known as insect growth regulators (IGRs). Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference).

In one embodiment the IGR is a compound that mimics juvenile hormone. Examples of juvenile hormone mimics include azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridizine-3(2H)-one Examples of IGRs suitable for use include but are not limited to methoprene, pyriproxyfen, hydroprene, cyromazine, fluazuron, lufenuron, novaluron, pyrethroids, 1-(2,6-difluorobenzoyl)-3-(2-fluoro-4-(trifluoromethyl)phenylurea, and novaluron.

In one embodiment, the compositions of the invention comprise an indole compound of formula (I) in combination with methoprene and a pharmaceutically acceptable carrier.

In another embodiment, the IGR compound is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, 1-(2,6-difluorobenzoyl)-3-(2-fluoro-4-(trifluoromethyl)phenylurea, 1-(2,6-difluorobenzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

In another embodiment, the compositions of the invention may comprise an indole compound of formula (I) in combination with a formamidine active agent including, but not limited to, amitraz.

In yet another embodiment of the invention, adulticide insecticides and acaricides can also be added to the composition of the invention. These include pyrethrins (which include cinerin I, cinerin II, jasmolin I, jasmolin II, pyrethrin I, pyrethrin II and mixtures thereof) and pyrethroids including permethrin, deltamethrin, cyfluthrin, flumethrin, cypermethrin and alpha cypermethrin; and carbamates (which include but are not limited to benomyl, carbanolate, carbaryl, carbofuran, meththiocarb, metolcarb, promacyl, propoxur, aldicarb, butocarboxim, oxamyl, thiocarboxime and thiofanox).

In some embodiments, the compositions of the invention may include one or more antinematodal agents including, but not limited to, active agents in the benzimidazoles, imidazothiazoles, tetrahydropyrimidines, organophosphates class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions may include an imidazothiazole compounds including, but not limited to, tetramisole, levamisole and butamisole. In still other embodiments, the compositions of the invention may include tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the invention may include other antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin and paromomycin II.

In another embodiment of the invention, the compositions may include a spinosyn active agent produced by the soil actinomycete *Saccharopolyspora spinosa* (see, for example Salgado V. L. and Sparks T. C., "The Spinosyns: Chemistry, Biochemistry, Mode of Action, and Resistance," in Comprehensive Molecular Insect Science, vol. 6, pp. 137-173, 2005) or a semi-synthetic spinosoid active agent. The spinosyns are typically referred to as factors or components A, B, C, D, E, F, G, H, J, K, L, M, N, 0, P, Q, R, S, T, U, V, W, or Y, and any of these components, or a combination thereof, may be used in the compositions of the invention. The spinosyn compound may be a 5,6,5-tricylic ring system, fused to a 12-membered macro cyclic lactone, a neutral sugar (rhamnose), and an amino sugar (forosamine). These and other natural spinosyn compounds, including 21-butenyl spinosyn produced by *Saccharopolyspora pagona*, which may be used in the compositions of the invention, may be produced via fermentation by conventional techniques known in the art. Other spinosyn compounds that may be used in the compositions of the invention are disclosed in U.S. Pat. Nos. 5,496,931; 5,670,364; 5,591,606; 5,571,901; 5,202,242; 5,767,253; 5,840,861; 5,670,486; 5,631,155 and 6,001,981, all incorporated by reference herein in their entirety. The spinosyn compounds may include, but are not limited to, spinosyn A, spinosyn D, spinosad, spinetoram, or combinations thereof. Spinosad is a combination of spinosyn A and spinosyn D, and spinetoram is a combination of 3'-ethoxy-5,6-dihydro spinosyn J and 3'-ethoxy spinosyn L.

In yet other embodiments, the compositions of the invention may include other active agents that are effective against arthropod parasites. Suitable active agents include, but are not limited to, bromocyclen, chlordane, DDT, endosulfan, lindane, methoxychlor, toxaphene, bromophos, bromophosethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a (4H)-dibenzofurancarboxaldehyde (MGK-11), 2-(2-ethylhexyl)-3a,4,7,7a-tetrahydro-4,7-methano-1H-isoindole-1,3

(2H)dione (MGK-264), dipropyl-2,5-pyridinedicarboxylate (MGK-326) and 2-(octylthio)ethanol (MGK-874).

An antiparasitic agent that can be combined with the compounds of the invention to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside (see Willson et al., *Parasitology*, January 2003, 126(Pt 1):79-86).

In one embodiment of the invention, arylpyrazole compounds such as phenylpyrazoles may be included in the veterinary compositions of the invention. The arylpyrazoles are known in the art and are suitable for combination with the isoxazoline compounds in the soft chewable compositions of the invention. Examples of such arylpyrazole compounds include but are not limited to those described in U.S. Pat. Nos. 6,001,384; 6,010,710; 6,083,519; 6,096,329; 6,174,540; 6,685,954, 6,998,131 and 7,759,381 (all of which are incorporated herein by reference). A particularly preferred arylpyrazole active agent is fipronil.

An insecticidal agent that can be combined with the compounds of the invention to form a composition can be a substituted pyridylmethyl derivative compound such as imidacloprid. Agents of this class are described above, and for example, in U.S. Pat. No. 4,742,060 or in EP 0 892 060. It would be well within the skill level of the practitioner to decide which individual compound can be used in the inventive formulation to treat a particular infection of an insect.

In certain embodiments, an insecticidal agent that can be combined with the compositions of the invention is a semicarbazone, such as metaflumizone.

In another embodiment, the compositions of the invention may advantageously include one or more isoxazoline compounds known in the art. These active agents are described in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 and WO 2008/122375, all of which are incorporated herein by reference in their entirety.

In another embodiment of the invention, nodulisporic acid and its derivatives (a class of known acaricidal, anthelmintic, anti-parasitic and insecticidal agents) may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in WO 2004/024704; Sager et al., Veterinary Parasitology, 2009, 159, 49-54; Kaminsky et al., Nature vol. 452, 13 Mar. 2008, 176-181. The compositions of the invention may also include aryloazol-2-yl cyanoethylamino compounds such as those described in US 2008/0312272 to Soll et al., which is incorporated herein in its entirety, and thioamide derivatives of these compounds, as described in U.S. patent application Ser. No. 12/582,486, filed Oct. 20, 2009, which is incorporated herein by reference.

The compositions of the invention may also be combined with paraherquamide compounds and derivatives of these compounds, including derquantel (see Ostlind et al., Research in Veterinary Science, 1990, 48, 260-61; and Ostlind et al., *Medical and Veterinary Entomology*, 1997, 11, 407-408). The paraherquamide family of compounds are known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. No. 5,703,078 and U.S. Pat. No. 5,750,695, all of which are hereby incorporated by reference in their entirety.

Dosage forms may contain from about 0.5 mg to about 5 g of a combination of active agents. In one embodiment of the dosage form, the amount of active is present in an amount of from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

Methods of Treatment

In another aspect, the invention is a method for treating helminth infestation comprising administration of an anthelmintically effective amount of a compound according to Formula (I) to an animal in need thereof. In one embodiment, the helminths are trematodes. In another embodiment, the helminths are the liver fluke *Fasciola hepatica*.

In one embodiment of the invention, methods for the treatment or prevention of a parasitic infestation or infection in a domestic animal are provided, which comprise administering an oral, topical or injectable composition comprising an effective amount of at least one indole active agent to the animal. The compositions and methods of the invention are effective against endoparasites, trematodes in particular, of animals and humans.

In one embodiment, the invention provides methods for the treatment and prevention of parasitic infections and infestations of animals (either wild or domesticated), including livestock and companion animals such as cats, dogs, horses, sheep, goats, pigs and cattle, with the aim of ridding these hosts of liver flukes commonly encountered by such animals.

By "treating" or "treat" or "treatment" is intended the application or administration of a composition of the invention to an animal that has a parasitic infestation for the eradication of the parasite or the reduction of the number of the parasites infesting the animal undergoing treatment. It is noted that the compositions of the invention may be used to prevent such a parasitic infestation.

Additional Active Agents

Additional veterinary/pharmaceutical active ingredients may be used in accordance with all embodiments and aspects detailed above.

In general, the additional active agent is included in the composition in an amount of between about 0.1 μg and about 1000 mg. More typically, the additional active agent may be included in an amount of about 10 µg to about 500 mg, about 1 mg to about 300 mg, about 10 mg to about 200 mg or about 10 mg to about 100 mg.

In other embodiments of the invention, the additional active agent may be included in the composition to deliver a dose of about 5 µg/kg to about 50 mg/kg per weight of the animal. In other embodiments, the additional active agent may be present in an amount sufficient to deliver a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 µg/kg to about 200 µg/kg or about 0.1 mg/kg to about 1 mg/kg of weight of animal. In still another embodiment of the invention, the additional active agent is included in a dose between about 0.5 mg/kg to about 50 mg/kg.

Optionally, a fragrance may be added to any of the compositions of the invention. Fragrances which are useful for the invention include but are not limited to:
(i) carboxylic acid esters such as octyl acetate, isoamyl acetate, isopropyl acetate and isobutyl acetate;
(ii) fragrant oils such as lavender oil.

The compositions of the invention are made by mixing the appropriate amount of the active agents, pharmaceutically acceptable carrier or diluent and optionally a crystallization inhibitor, antioxidant, preservative, film former, etc., to form a composition of the invention. In some embodiments the composition can be obtained by following the method of making these forms described above by the description of making these forms found in general formulation text known to those in the art, e.g., *Remington—The Science and Practice of Pharmacy* (21$^{st}$ Edition) (2005), *Goodman & Gilman's The Pharmacological Basis of Therapeutics* (11$^{th}$ Edition) (2005) and *Ansel's Pharmaceutical Dosage Forms and Drug Delivery Systems* (8$^{th}$ Edition), edited by Allen et al., *Lippincott Williams & Wilkins*, (2005).

The inventive formulations may contain other inert ingredients such as antioxidants, preservatives, or pH stabilizers. These compounds are well known in the formulation art. Antioxidants such as an alpha tocopherol, ascorbic acid, ascorbyl palmitate, fumaric acid, malic acid, sodium ascorbate, sodium metabisulfate, n-propyl gallate, BHA (butylated hydroxy anisole), BHT (butylated hydroxy toluene) monothioglycerol and the like, may be added to the present formulation. The antioxidants are generally added to the formulation in amounts of from about 0.01 to about 2.0%, based upon total weight of the formulation, such as about 0.05% to about 1.0%.

Preservatives, such as the parabens (methylparaben and/or propylparaben), are suitably used in the formulation in amounts ranging from about 0.01% to about 2.0%, or about 0.05% to about 1.0%. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Ranges for these compounds include from about 0.01% to about 5%.

Compounds which stabilize the pH of the formulation are also contemplated. Again, such compounds are well known to a practitioner in the art as well as how to use these compounds. Buffering systems include, for example, systems selected from the group consisting of acetic acid/acetate, malic acid/malate, citric acid/citrate, tartaric acid/tartrate, lactic acid/lactate, phosphoric acid/phosphate, glycine/glycimate, tris, glutamic acid/glutamates or sodium carbonate.

The compositions of the invention are administered in parasiticidally effective amounts which are suitable to control the parasite in question to the desired extent, as described below. In each aspect of the invention, the compounds and compositions of the invention can be applied against a single pest or combinations thereof.

The compositions of the invention may be administered continuously, for treatment or prevention of parasitic infections or infestations. In this manner, the compositions of the invention deliver an effective amount of the active compounds to the animal in need thereof to control the target parasites. By "effective amount" is intended a sufficient amount of a composition of the invention to eradicate or reduce the number of parasites infesting the animal.

In some embodiments, an effective amount of the active agent achieves at least 70% efficacy against the target parasite. In other embodiments, an effective amount of the active agent achieves at least 80%, or at least 90% efficacy against the target pests. In other embodiments, an effective amount of the active agent will achieve at least 95%, at least 98% or 100% efficacy against the target parasites.

Generally, a dose of from about 0.001 to about 100 mg per kg of body weight given as a single dose or in divided doses for a period of from 1 to 5 days will be satisfactory, but there can be instances where higher or lower dosage ranges are indicated, and such are within the scope of this invention. It is well within the routine skill of the practitioner to determine a particular dosing regimen for a specific host and parasite.

Higher amounts may be provided for very prolonged release in or on the body of the animal. In another treatment embodiment, the amount of active agents for animals which are small in size is greater than about 0.01 mg/kg, and in another embodiment for the treatment of small-sized animals the amount of active agents is between about 0.01 and about 20 mg/kg of weight of animal.

The solutions according to the invention may be applied using any means known per se, e.g., using an applicator gun or a metering flask, pipette, syringes, roll on, droppers, capsules, foil packages, vials, twist tip containers and other single dose and multi-dose containers.

In another aspect of the invention, a kit for the treatment or prevention of a parasitic infestation in an animal is provided, which comprises at least one isoxazoline active agent together with a pharmaceutically acceptable carrier and a dispensing device for topical application of the composition. The dispensing device may be a pipette, syringes, roll on, droppers, capsules, foil packages, vials, twist tip containers and other single dose and multi-dose containers, which includes an effective dose of each active agent in the pharmaceutically acceptable carrier or diluent.

An important aspect of the invention is to provide a multiple-use container comprising a topical composition of the invention, from which accurate single dose aliquots of the long lasting topical formulations may be administered. The formulation must remain stable with repetitive exposure to the outside environment, particularly oxygen and water. This embodiment may be particularly useful with the very long lasting formulations of the invention that require administration to an animal infrequently, such as once every 3-6 months, or similar. Some solvents such as ethers (including DMI (dimethyl isosorbide) and the like) give rise to peroxides, which then yield ketones and aldehydes that may be further degraded to acids. The presence of acids may contribute to the degradation of acid hydrolysis-susceptible molecules. Thus, formulation stability is particularly important for the multi-dose container application, where the formulations can be exposed to oxygen and water during multiple rounds of opening and closing. Importantly, it was found that the use of certain antioxidants such as BHT and BHA efficiently inhibit the degradation of the active agent in ether solvents. For example, a 12% (w/v) solution of an indole compound of the invention in DMI exhibited no significant change in assay over the course of an eleven week accelerated stability study at 50° C. in clear glass containers.

EXAMPLES

The invention is further described by the following non-limiting examples which further illustrate the invention and are not intended (nor should they be interpreted to) limit the scope of the invention.

Compound number 332 (i.e., 5-[2-chloro-4-(trifluoromethyl)phenyl]-2-(trifluoromethyl)-1H-indole) was prepared as follows.

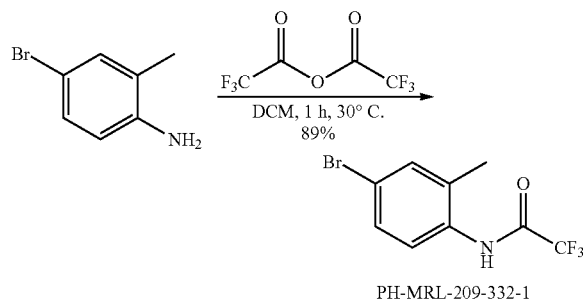

Into a 500-mL round-bottom flask, was placed 4-bromo-2-methylaniline (10 g, 53.75 mmol, 1.00 equiv), dichloromethane (150 mL), trifluoroacetyl 2,2,2-trifluoroacetate (13.6 g, 64.75 mmol, 1.20 equiv). The resulting solution was stirred for 1 h at 30° C. The resulting mixture was concentrated under vacuum. This resulted in 15 g (89%) of N-(4-bromo-2-methylphenyl)-2,2,2-trifluoroacetamide as a white solid.

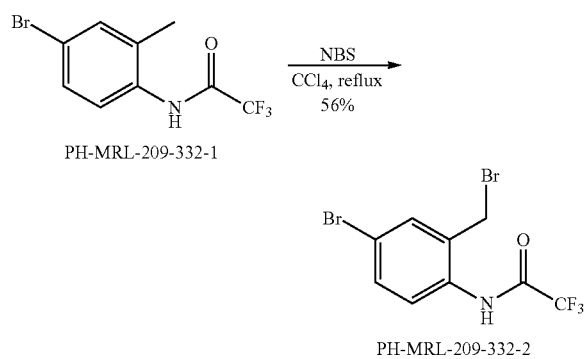

Next, into a 50-mL round-bottom flask, was placed N-(4-bromo-2-methylphenyl)-2,2,2-trifluoroacetamide (100 mg, 0.35 mmol, 1.00 equiv), CCl₄ (3 mL), NBS (63 mg, 0.35 mmol, 1.00 equiv). The resulting solution was heated to reflux for 6 h under a 100 watt incandescent bulb and a infrared bub. The resulting mixture was concentrated under vacuum. The residue was applied onto a silica gel column with PE/EA (petroleum ether/ethyl acetate, 8:1). This resulted in 80 mg (56%) of N-[4-bromo-2-(bromomethyl)phenyl]-2,2,2-trifluoroacetamide as a white solid.

$^1$H NMR (400 MHz, CDCl$_3$) δ: 7.83 (d, J=8.4 Hz, 1H), 7.55-~7.62 (m, 2H), 4.44 (s, 3H).

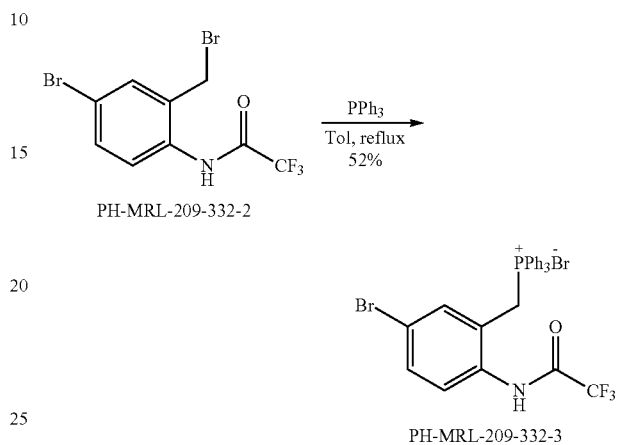

Next, into a 100-mL round-bottom flask, was placed N-[4-bromo-2-(bromomethyl)phenyl]-2,2,2-trifluoroacetamide (600 mg, 1.66 mmol, 1.00 equiv), tol (10 mL), PPh$_3$ (437 mg, 1.67 mmol, 1.00 equiv). The resulting solution was stirred for 3 h at 70° C. The solids were collected by filtration. This resulted in 600 mg (52%) of [[5-bromo-2-(trifluoroacetamido)phenyl]methyl]triphenylphosphonium bromide as a white solid.

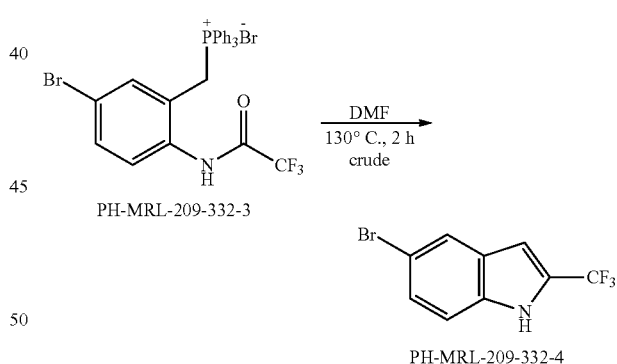

Next, into a 50-mL round-bottom flask, was placed [[5-bromo-2-(trifluoroacetamido)phenyl]methyl]triphenylphosphonium bromide (400 mg, 0.64 mmol, 1.00 equiv), N,N-dimethylformamide (10 mL), TEA (triethylamine, 324 mg, 3.20 mmol, 5.00 equiv). The resulting solution was stirred for 2 h at 130° C. The reaction was then quenched by the addition of 10 ml of water. The resulting solution was extracted with 3×10 mL of ethyl acetate and the organic layers combined. The resulting mixture was washed with 3×20 mL of brine. The mixture was dried over anhydrous sodium sulfate and concentrated under vacuum. This resulted in 300 mg (crude) of 5-bromo-2-(trifluoromethyl)-1H-indole as brown oil.

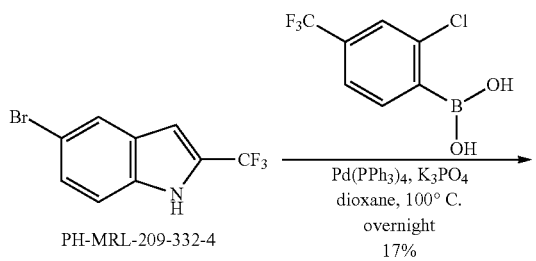

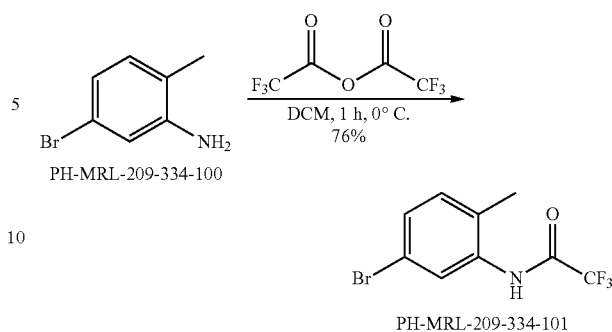

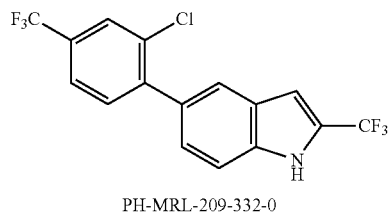

Finally, into a 50-mL round-bottom flask purged and maintained with an inert atmosphere of nitrogen, was placed 5-bromo-2-(trifluoromethyl)-1H-indole (100 mg, 0.38 mmol, 1.00 equiv), dioxane (5 mL), [2-chloro-4-(trifluoromethyl)phenyl]boronic acid (169 mg, 0.75 mmol, 1.99 equiv), Pd(PPh$_3$)$_4$ (43 mg, 0.04 mmol, 0.10 equiv), K$_3$PO$_4$ (240 mg, 1.13 mmol, 2.99 equiv), water (0.5 mL). The resulting solution was stirred overnight at 100° C. The reaction was then quenched by the addition of 10 ml of water. The resulting solution was extracted with 3×10 mL of ethyl acetate and the organic layers combined. The resulting mixture was washed with 3×10 ml, of brine. The resulting mixture was concentrated under vacuum. The residue was applied onto a TLC plate with PE/EA (10:1). This resulted in 26.6 mg (17%) of 5-[2-chloro-4-(trifluoromethyl)phenyl]-2-(trifluoromethyl)-1H-indole as light yellow oil. (ES, m/z): [M−H]$^-$ 362; $^1$H NMR (400 MHz, CDCl$_3$) δ: 7.80 (s, 1H), 7.72 (s, 1H), 7.53-~7.68 (m, 3H), 7.47 (d, J=6.0 Hz, 1H), 6.95 (s, 1H).

Compound number 334 (i.e., 6-[2-chloro-4-(trifluoromethyl)phenyl]-2-(trifluoromethyl)-1H-indole) was prepared as follows.

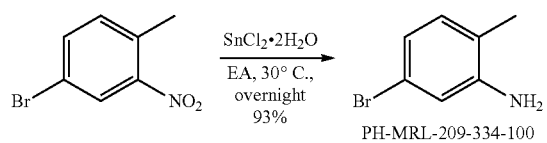

First, into a 250-mL round-bottom flask, was placed 4-bromo-1-methyl-2-nitrobenzene (5 g, 23.14 mmol, 1.00 equiv), ethyl acetate (100 mL), SnCl$_2$.H$_2$O (20 g). The resulting solution was stirred overnight at 30° C. The pH value of the solution was adjusted to 10 with sodium hydroxide (5 mol/L). The resulting solution was extracted with 3×30 mL of ethyl acetate and the organic layers combined. The resulting mixture was washed with 3×50 mL of brine. The organic phase was dried over anhydrous sodium sulfate and concentrated under vacuum. This resulted in 4 g (93%) of 5-bromo-2-methylaniline as brown oil.

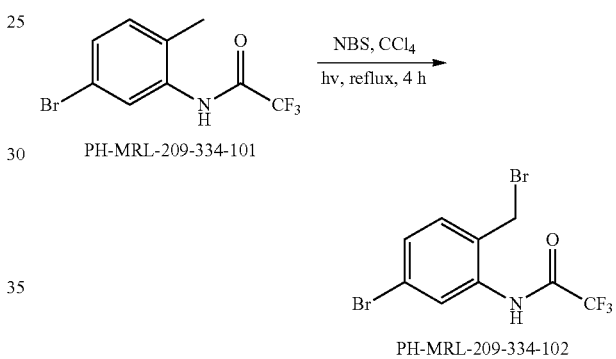

Next, into a 100-mL round-bottom flask, was placed 5-bromo-2-methylaniline (2 g, 10.75 mmol, 1.00 equiv), dichloromethane (40 mL), trifluoroacetyl 2,2,2-trifluoroacetate (2.7 g, 12.86 mmol, 1.20 equiv). The resulting solution was stirred for 1 h at 0° C. The resulting mixture was concentrated under vacuum. This resulted in 2.3 g (76%) of N-(5-bromo-2-methylphenyl)-2,2,2-trifluoroacetamide as a light brown solid.

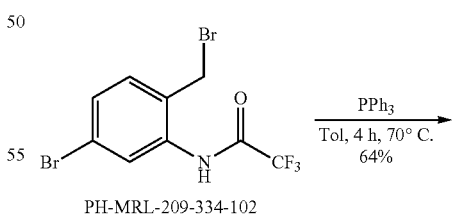

Next, into a 100-mL round-bottom flask, was placed N-(5-bromo-2-methylphenyl)-2,2,2-trifluoroacetamide (500 mg, 1.77 mmol, 1.00 equiv), CCl$_4$ (10 mL), NBS (315 mg, 1.77 mmol, 1.00 equiv). The resulting solution was heated to reflux for 4 h under a 100 watt incandescent bulb. The solids were filtered out. The resulting mixture was concentrated under vacuum. This resulted in 600 mg (crude) of N-[5-bromo-2-(bromomethyl)phenyl]-2,2,2-trifluoroacetamide as a light yellow solid.

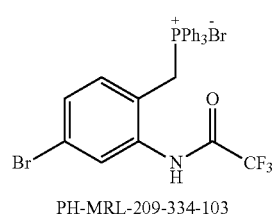

Next, into a 100-mL round-bottom flask, was placed N-[5-bromo-2-(bromomethyl)phenyl]-2,2,2-trifluoroacetamide (600 mg, 1.66 mmol, 1.00 equiv), tol (10 mL), PPh₃ (435 mg, 1.66 mmol, 1.00 equiv). The resulting solution was stirred for 4 h at 70° C. The solids were collected by filtration and washed with EA 10 ml*2. This resulted in 700 mg (64%) of [[4-bromo-2-(trifluoroacetamido)phenyl]methyl]triphenylphosphonium bromide as a white solid.

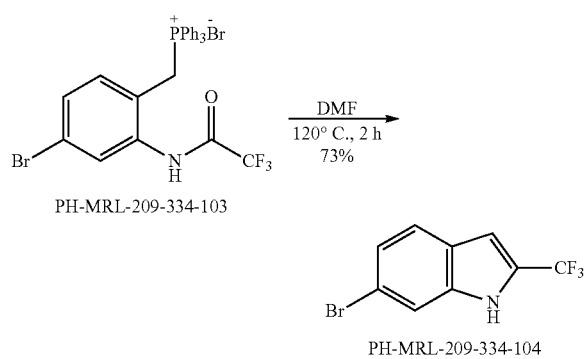

Next, into a 50-mL round-bottom flask, was placed [[4-bromo-2-(trifluoroacetamido)phenyl]-methyl]triphenylphosphonium bromide (350 mg, 0.56 mmol, 1.00 equiv), N,N-dimethylformamide (10 mL), TEA (567 mg, 5.60 mmol, 9.98 equiv). The resulting solution was stirred for 2 h at 120° C. The reaction was then quenched by the addition of 10 ml of water. The resulting solution was extracted with 3×10 mL of ethyl acetate and the organic layers combined. The resulting mixture was washed with 3×20 mL of brine. The organic phase was dried over anhydrous sodium sulfate and concentrated under vacuum. This resulted in 120 mg (73%) of 6-bromo-2-(trifluoromethyl)-1H-indole as brown oil.

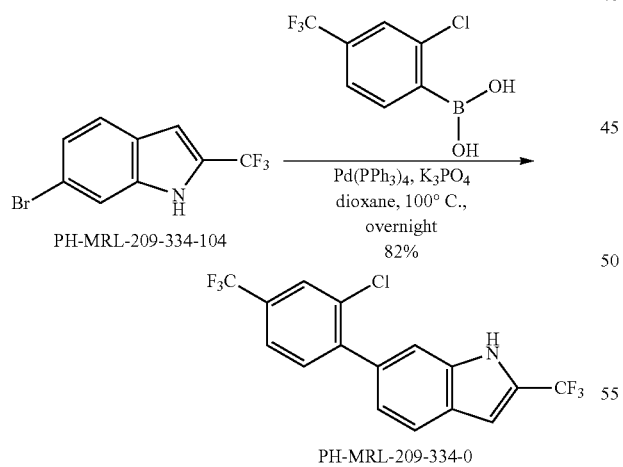

Finally, into a 50-mL round-bottom flask purged and maintained with an inert atmosphere of nitrogen, was placed 6-bromo-2-(trifluoromethyl)-1H-indole (80 mg, 0.30 mmol, 1.00 equiv), dioxane (5 mL), [2-chloro-4-(trifluoromethyl)phenyl]boronic acid (135 mg, 0.60 mmol, 1.99 equiv), Pd(PPh₃)₄ (34.9 mg, 0.03 mmol, 0.10 equiv), K₃PO₄ (192 mg, 0.90 mmol, 2.99 equiv), water (0.5 mL). The resulting solution was stirred overnight at 100° C. The reaction was then quenched by the addition of 10 ml of water. The resulting solution was extracted with 3×10 mL of ethyl acetate and the organic layers combined. The resulting mixture was washed with 3×10 mL of brine. The resulting mixture was concentrated under vacuum. The residue was applied onto a TLC plate with PE/EA (10/1). This resulted in 113 mg (92%) of 6-[2-chloro-4-(trifluoromethyl)phenyl]-2-(trifluoromethyl)-1H-indole as yellow oil. (ES, m/z): [M−H]⁻ 362; ¹H NMR (400 MHz, CDCl₃) δ: 7.84 (s, 1H), 7.63-7.77 (m, 3H), 7.55 (s, 1H), 7.22 (d, J=7.5 Hz, 1H), 6.97 (s, 1H).

Compound number 336 (i.e., 6-chloro-5-[2-chloro-4-(trifluoromethyl)phenyl]-2-(trifluoromethyl)-1H-indole) was made as follows.

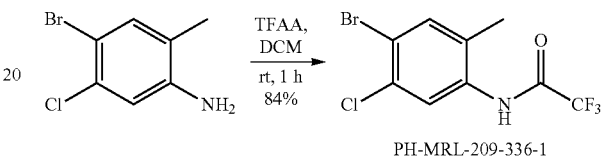

First, into a 500-mL 3-necked round-bottom flask purged and maintained with an inert atmosphere of nitrogen, was placed dichloromethane (400 mL), 4-bromo-5-chloro-2-methylaniline (25 g, 113.38 mmol, 1.00 equiv). This was followed by the addition of TFAA (trifluoroacetic anhydride, 27.4 g, 130.46 mmol, 1.15 equiv) dropwise with stirring at 0° C. in a water/ice bath. The resulting solution was allowed to react, with stirring, for an additional 1 h at room temperature. The resulting mixture was concentrated under vacuum. This resulted in 30 g (84%) of N-(4-bromo-5-chloro-2-methylphenyl)-2,2,2-trifluoroacetamide as a white solid.

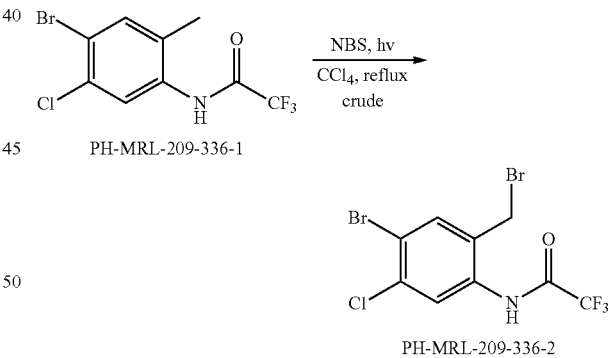

Next, into a 500-mL round-bottom flask purged and maintained with an inert atmosphere of nitrogen, was placed CCl₄ (300 mL), N-(4-bromo-5-chloro-2-methylphenyl)-2,2,2-trifluoroacetamide (15 g, 47.39 mmol, 1.00 equiv), NBS (8 g, 44.95 mmol, 0.95 equiv). The resulting solution was stirred for 4 h at 80° C. with infrared light and initiated by light. This reaction was repeated for 1 times. Then the reaction mixture was cooled. The solids were filtered out and washed with enough CCl₄. The filtrate was concentrated under vacuum. This resulted in 40 g (crude) of N-[4-bromo-2-(bromomethyl)-5-chlorophenyl]-2,2,2-trifluoroacetamide as a brown solid.

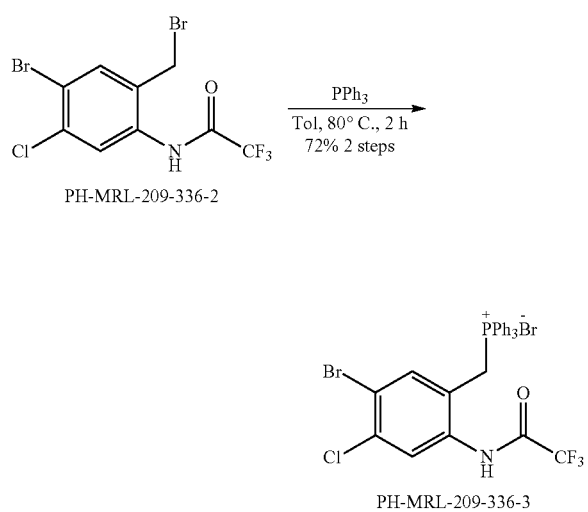

PH-MRL-209-336-2

PH-MRL-209-336-3

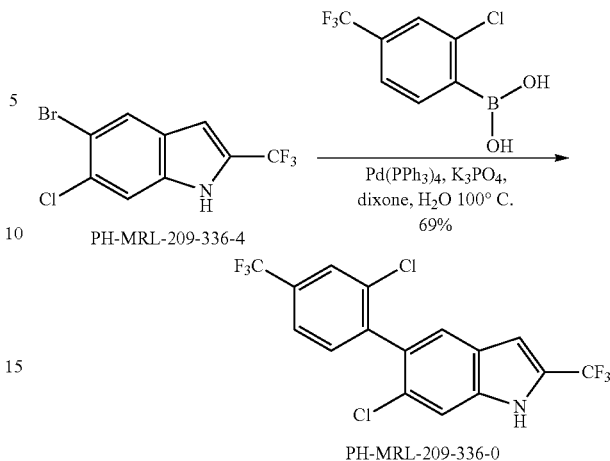

PH-MRL-209-336-4

PH-MRL-209-336-0

Next, into a 1-L round-bottom flask purged and maintained with an inert atmosphere of nitrogen, was placed toluene (800 mL), N-[4-bromo-2-(bromomethyl)-5-chlorophenyl]-2,2,2-trifluoroacetamide (40 g, 101.16 mmol, 1.00 equiv), PPh₃ (29.5 g, 112.47 mmol, 1.20 equiv). The resulting solution was stirred for 2 h at 80° C. in an oil bath. The reaction mixture was cooled.

The solids were collected by filtration, and washed with enough EA. Then the solid was dried under infrared light. This resulted in 45 g (68%) of [[5-bromo-4-chloro-2-(trifluoroacetamido)phenyl]methyl]triphenylphosphonium bromide as a white solid.

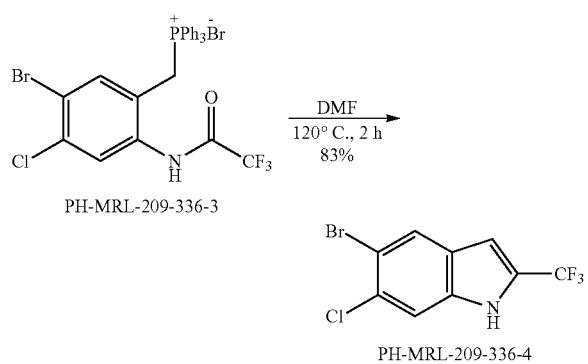

PH-MRL-209-336-3

PH-MRL-209-336-4

Next, into a 1-L round-bottom flask, was placed N,N-dimethylformamide (600 mL), [[5-bromo-4-chloro-2-(trifluoroacetamido)phenyl]methyl]triphenylphosphonium bromide (45 g, 68.42 mmol, 1.00 equiv), TEA (34 g, 336.00 mmol, 5.00 equiv). The resulting solution was stirred for 2 h at 120° C. in an oil bath. The reaction mixture was cooled. The reaction mixture was poured into 1.5 L of water/ice. The resulting solution was extracted with 3×700 mL of ethyl acetate and the organic layers combined. The resulting mixture was washed with 3×600 mL of brine. The organic phase was concentrated under vacuum. The residue was applied onto a silica gel column with ethyl acetate/petroleum ether (1:10). This resulted in 17 g (83%) of 5-bromo-6-chloro-2-(trifluoromethyl)-1H-indole as a white solid.

Finally, into a 250-mL 3-necked round-bottom flask purged and maintained with an inert atmosphere of nitrogen, was placed dioxane (120 mL), water (20 mL), 5-bromo-6-chloro-2-(trifluoromethyl)-1H-indole (6 g, 20.10 mmol, 1.00 equiv), [2-chloro-4-(trifluoromethyl)phenyl]boronic acid (9 g, 40.11 mmol, 2.00 equiv), K₃PO₄ (12.7 g, 59.83 mmol, 3.00 equiv), Pd(PPh₃)₄ (1.85 g, 1.60 mmol, 0.08 equiv). The resulting solution was stirred overnight at 100° C. in an oil bath. This reaction was repeated for 1 times. The reaction mixture was cooled. The resulting solution was diluted with 300 mL of ethyl acetate. The resulting mixture was washed with 3×80 mL of brine. The resulting mixture was concentrated under vacuum. The residue was applied onto a silica gel column with dichloromethane. This resulted in 11.0 g (69%) of 6-chloro-5-[2-chloro-4-(trifluoromethyl)phenyl]-2-(trifluoromethyl)-1H-indole as a white solid. LC-MS-PH-MRL-209-336-0: (ES, m/z): 396[M–H]⁻ H-NMR-PH-MRL-209-336-0: (300 MHz, DMSO, ppm): δ 12.65 (s, 1H), 8.02 (s, 1H), 7.83 (d, J=9.0 Hz, 1H), 7.71 (d, J=9.0 Hz, 2H), 7.62~7.65 (d, J=9.0 Hz, 1H), 7.14 (s, 1H).

Compound number 337 (i.e., 6-chloro-5-[2-chloro-4-(trifluoromethyl)phenyl]-2-methyl-1H-indole) was made as follows.

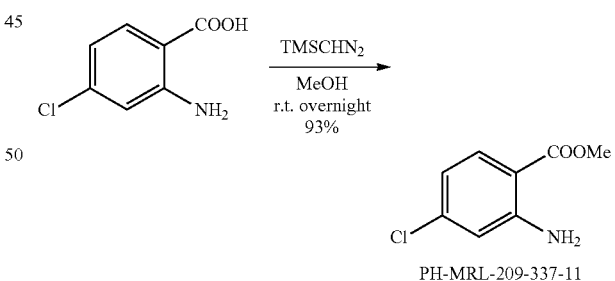

PH-MRL-209-337-11

First, into a 500-mL 3-necked round-bottom flask purged and maintained with an inert atmosphere of nitrogen, was placed methanol/DCM (150/100 mL), 2-amino-4-chlorobenzoic acid (10 g, 58.28 mmol, 1.00 equiv). This was followed by the addition of TMSCHN₂ (30.7 mL, 1.05 equiv) dropwise with stirring at 0° C. The resulting solution was stirred overnight at room temperature. The resulting mixture was concentrated under vacuum. The resulting mixture was washed with 1×20 mL of n-hexane. This resulted in 10.1 g (93%) of methyl 2-amino-4-chlorobenzoate as a yellow solid.

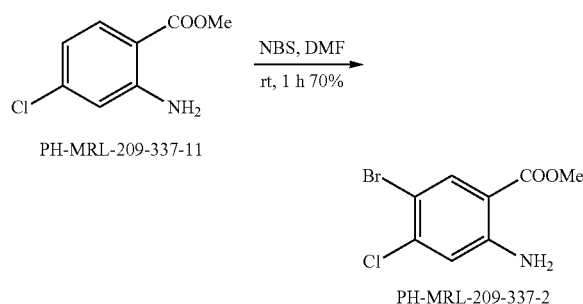

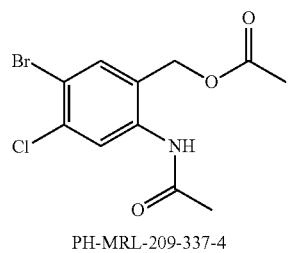

Next, into a 250-mL 3-necked round-bottom flask, was placed N,N-dimethylformamide (200 mL), methyl 2-amino-4-chlorobenzoate (8 g, 43.10 mmol, 1.00 equiv), NBS (7.7 g, 1.00 equiv). The resulting solution was stirred for 1 h at room temperature. The resulting solution was diluted with 600 mL of ice/water. The resulting solution was extracted with 3×200 mL of ethyl acetate and the organic layers combined. The resulting mixture was washed with 3×150 mL of Brine. The resulting organic phase was concentrated under vacuum. The solid was washed with 4 mL/20 mL of ether/hexane. The solid was dried in an oven under reduced pressure. This resulted in 8.0 g (70%) of methyl 2-amino-5-bromo-4-chlorobenzoate as a pink solid.

Next, into a 50-mL 3-necked round-bottom flask purged and maintained with an inert atmosphere of nitrogen, was placed tetrahydrofuran (30 mL), (2-amino-5-bromo-4-chlorophenyl)methanol (1.27 g, 5.37 mmol, 1.00 equiv), TEA (1.35 g, 13.34 mmol, 2.50 equiv). This was followed by the addition of acetyl chloride (880 mg, 11.21 mmol, 2.10 equiv) dropwise with stirring at 0° C. The resulting solution was stirred for 0.5 h at room temperature. And then the reaction mixture was prepared for the next step.

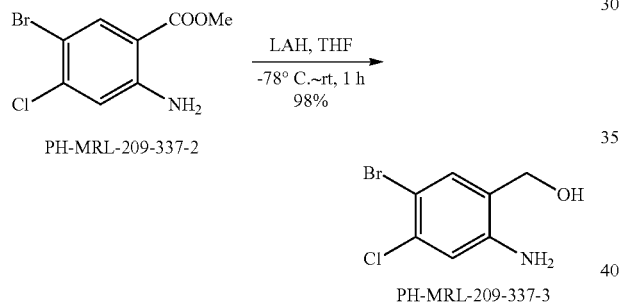

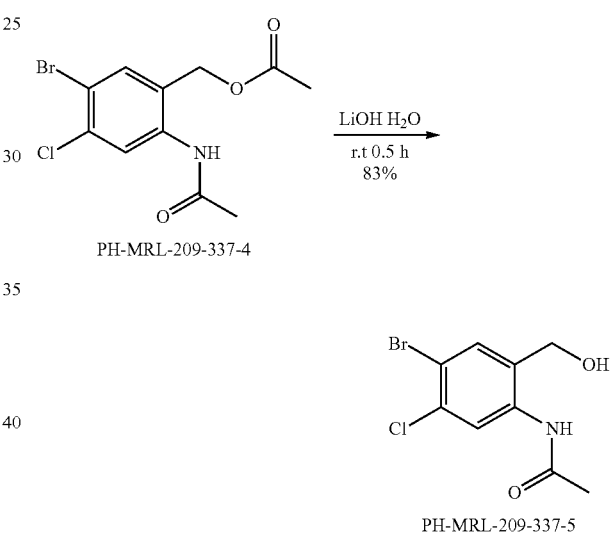

Next, into a 250-mL 3-necked round-bottom flask purged and maintained with an inert atmosphere of nitrogen, was placed tetrahydrofuran (200 mL). This was followed by the addition of LiAlH$_4$ (1.26 g, 37.14 mmol, 1.10 equiv), in portions. To this was added methyl 2-amino-5-bromo-4-chlorobenzoate (8 g, 30.25 mmol, 1.00 equiv) dropwise with stirring at −78° C. The resulting solution was stirred for 1 h at room temperature. The reaction was then quenched by the addition of 200 mL of water. The resulting solution was extracted with 3×150 mL of ethyl acetate and the organic layers combined. The resulting mixture was washed with 3×100 mL of brine. The organic phase was dried over anhydrous sodium sulfate and concentrated under vacuum. This resulted in 7 g (98%) of (2-amino-5-bromo-4-chlorophenyl)methanol as a light yellow solid.

Next, added the 10% LiPH/H$_2$O (10 mL) to step four reaction mixture. The resulting solution was stirred for 0.5 h at room temperature. The resulting solution was diluted with 30 mL of water and extracted with 3×20 mL of ethyl acetate and the organic layers combined. The resulting mixture was washed with 3×15 mL of Brine. The organic phase was dried over anhydrous sodium sulfate and concentrated under vacuum. This resulted in 1.3 g (83%) of N-[4-bromo-5-chloro-2-(hydroxymethyl)phenyl]acetamide as a white solid.

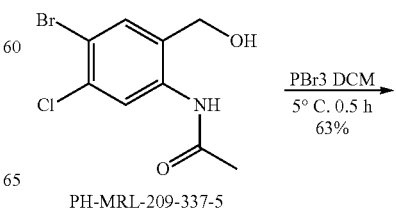

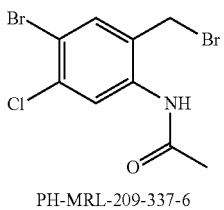

PH-MRL-209-337-6

Next, into a 50-mL 3-necked round-bottom flask purged and maintained with an inert atmosphere of nitrogen, was placed dichloromethane (30 g, 353.23 mmol, 75.68 equiv), N-[4-bromo-5-chloro-2-(hydroxymethyl)phenyl]acetamide (1.3 g, 4.67 mmol, 1.00 equiv). This was followed by the addition of tribromophosphane (490 mg, 1.81 mmol, 0.40 equiv) dropwise with stirring at 5° C. The resulting solution was stirred for 0.5 h at 5° C. The temperature was increased to room temperature naturally. The resulting solution was diluted with 50 mL of DCM. The reaction was then quenched by the addition of 1 mL of water. The resulting mixture was washed with 3×10 mL of Brine. The organic phase was dried over anhydrous sodium sulfate and concentrated under vacuum. This resulted in 1.3 g (63%) of N-[4-bromo-2-(bromomethyl)-5-chlorophenyl]acetamide as a white solid.

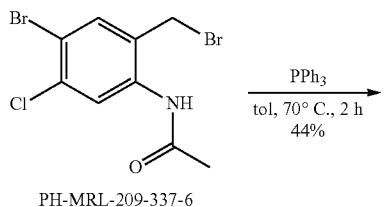

PH-MRL-209-337-6

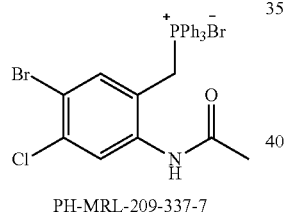

PH-MRL-209-337-7

Next, into a 50-mL round-bottom flask purged and maintained with an inert atmosphere of nitrogen, was placed toluene (30 mL), N-[4-bromo-2-(bromomethyl)-5-chlorophenyl]acetamide (1.3 g, 3.81 mmol, 1.00 equiv), triphenylphosphine (1.1 g, 4.19 mmol, 1.10 equiv). The resulting solution was stirred for 2 h at 70° C. in an oil bath. The reaction mixture was cooled to room temperature. The solids were collected by filtration and washed with enough EtOAc. The solid was dried in an oven under reduced pressure. This resulted in 1.0 g (44%) of [(5-bromo-4-chloro-2-acetamidophenyl)methyl]triphenylphosphonium bromide as a white solid.

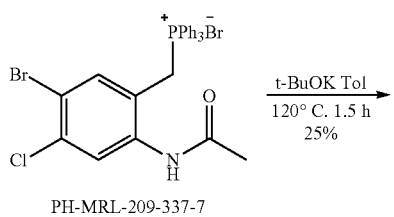

PH-MRL-209-337-7

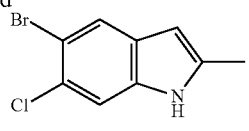

PH-MRL-209-337-8

Next, into a 50-mL round-bottom flask purged and maintained with an inert atmosphere of nitrogen, was placed toluene (30 mL), [(5-bromo-4-chloro-2-acetamidophenyl)methyl]triphenylphosphanium bromide (1.0 g, 1.66 mmol, 1.00 equiv). The reaction mixture was stirred at 120° C. in an oil bath, then added (tert-butoxy)potassium (740 mg, 6.59 mmol, 4.00 equiv) in two portions for 1.5 hours. The reaction mixture was cooled to room temperature. The resulting mixture was concentrated under vacuum. The residue was applied onto a silica gel column with ethyl acetate/petroleum ether (1:25-1:10). This resulted in 100 mg (25%) of 5-bromo-6-chloro-2-methyl-1H-indole as a white solid.

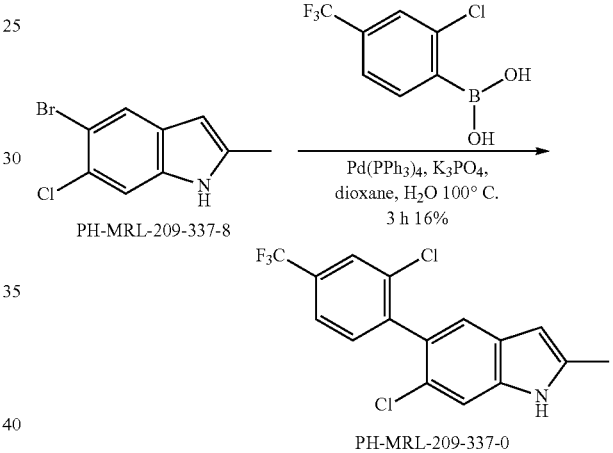

Finally, into a 100-mL round-bottom flask purged and maintained with an inert atmosphere of nitrogen, was placed dioxane (10 mL), water (2 mL), 5-bromo-6-chloro-2-methyl-1H-indole (100 mg, 0.41 mmol, 1.00 equiv), [2-chloro-4-(trifluoromethyl)phenyl]boronic acid (184 mg, 0.82 mmol, 2.00 equiv), $K_3PO_4$ (260 mg, 1.22 mmol, 3.00 equiv), $Pd(PPh_3)_4$ (47 mg, 0.04 mmol, 0.10 equiv). The resulting solution was stirred for 3 h at 100° C. in an oil bath. The reaction mixture was cooled to room temperature. The resulting solution was diluted with 40 mL of ethyl acetate. The resulting mixture was washed with 3×10 mL of Brine. The organic phase was dried over anhydrous sodium sulfate and concentrated under vacuum. The residue was purified by thin layer chromatography developed with ethyl acetate/PE (1:5) This resulted in 22.9 mg (16%) of 6-chloro-5-[2-chloro-4-(trifluoromethyl)phenyl]-2-methyl-1H-indole as a off-white solid. (ES, m/z): 342[M−H]⁻

H-NMR-PH-MRL-209-337-0: (300 MHz, DMSO, ppm): δ 11.23 (s, 1H), 7.97~8.00 (m, 1H), 7.78 (dd, J=1.2, 8.1 Hz, 1H), 7.59 (d, J=7.8 Hz, 1H), 7.45 (s, 1H), 7.35 (s, 1H), 6.18~6.19 (m, 1H), 2.40 (s, 3H).

Compound number 338 (i.e., 6-chloro-5-[2-chloro-4-(trifluoromethyl)phenyl]-2-ethyl-1H-indole) was made as follows.

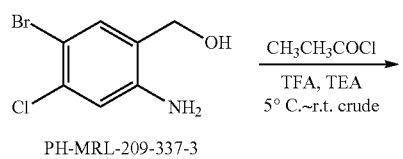

PH-MRL-209-337-3

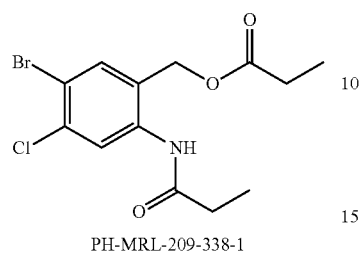

PH-MRL-209-338-1

First, into a 100-mL 3-necked round-bottom flask purged and maintained with an inert atmosphere of nitrogen, was placed tetrahydrofuran (50 mL), (2-amino-5-bromo-4-chlorophenyl)methanol (2 g, 8.46 mmol, 1.00 equiv), TEA (1.88 g, 18.58 mmol, 2.20 equiv). This was followed by the addition of propanoyl chloride (1.64 g, 17.73 mmol, 2.00 equiv) dropwise with stirring at 5° C. The resulting solution was stirred for 0.5 h at room temperature. Then the reaction mixture was prepared for the next step.

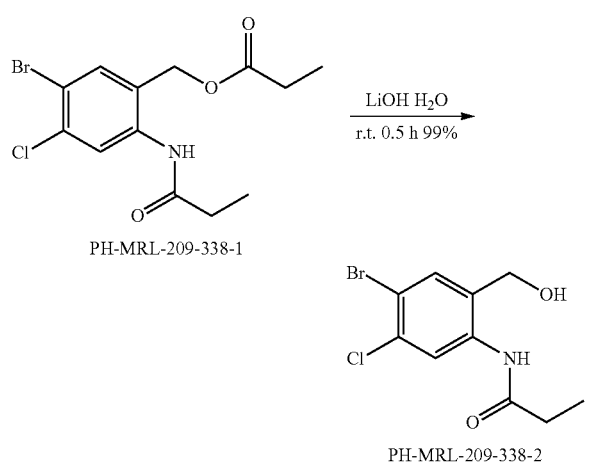

PH-MRL-209-338-1

PH-MRL-209-338-2

Next, 15% LiOH/H$_2$O (40 mL) was added to the step one reaction mixture. The resulting solution was stirred for 0.5 h at room temperature. The resulting solution was diluted with 100 mL of water and extracted with 3×100 mL of ethyl acetate and the organic layers combined. The resulting mixture was washed with 3×80 mL of Brine. The organic phase was dried over anhydrous sodium sulfate and concentrated under vacuum. This resulted in 2.5 g (99%) of N-[4-bromo-5-chloro-2-(hydroxymethyl)phenyl]-propanamide as a light yellow solid.

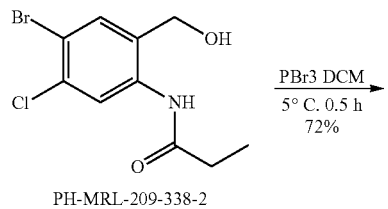

PH-MRL-209-338-2

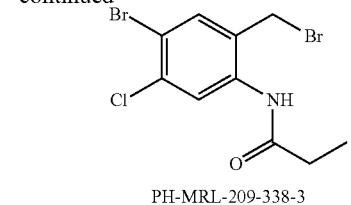

PH-MRL-209-338-3

Next, into a 100-mL 3-necked round-bottom flask purged and maintained with an inert atmosphere of nitrogen, was placed dichloromethane (40 mL), N-[4-bromo-5-chloro-2-(hydroxymethyl)phenyl]propanamide (1.6 g, 5.47 mmol, 1.00 equiv). This was followed by the addition of PBr$_3$ (570 mg, 2.11 mmol, 0.40 equiv) dropwise with stirring at 5° C. The resulting solution was stirred for 0.5 h at 5° C. The resulting solution was diluted with 50 mL of DCM. The reaction was then quenched by the addition of 1 mL of water. The resulting mixture was washed with 3×20 mL of Brine. The organic phase was dried over anhydrous sodium sulfate and concentrated under vacuum. This resulted in 1.4 g (72%) of N-[4-bromo-2-(bromomethyl)-5-chlorophenyl]propanamide as a light yellow solid.

PH-MRL-209-338-3

PH-MRL-209-338-4

Next, into a 50-mL round-bottom flask purged and maintained with an inert atmosphere of nitrogen, was placed toluene (30 mL), N-[4-bromo-2-(bromomethyl)-5-chlorophenyl]propanamide (1.4 g, 3.94 mmol, 1.00 equiv), triphenylphosphine (1.13 g, 4.31 mmol, 1.10 equiv). The resulting solution was stirred for 2 h at 70° C. in an oil bath. The reaction mixture was cooled to room temperature. The solids were collected by filtration, and the solid was washed with enough EtOAc. The solid was dried in an oven under reduced pressure. This resulted in 1.05 g (43%) of [(5-bromo-4-chloro-2-propanamidophenyl)methyl]triphenylphosphonium bromide as a white solid.

PH-MRL-209-338-4

-continued

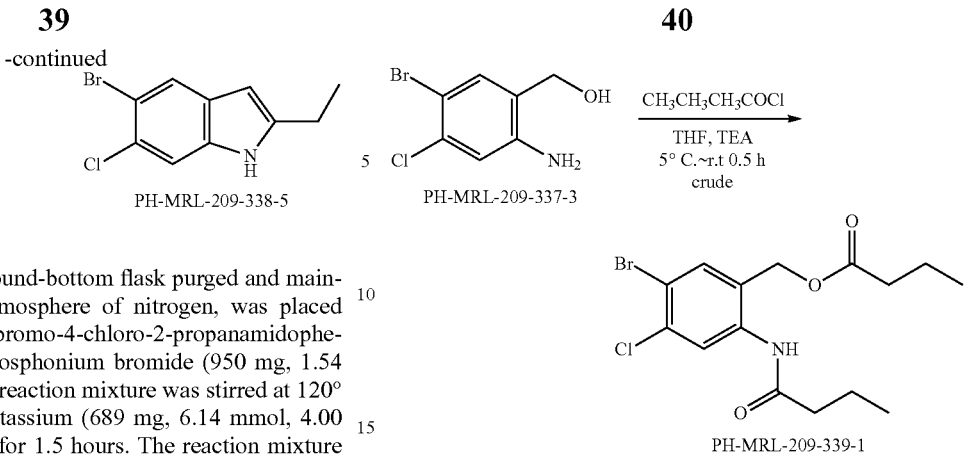

Next, into a 50-mL round-bottom flask purged and maintained with an inert atmosphere of nitrogen, was placed toluene (20 mL), [(5-bromo-4-chloro-2-propanamidophenyl)methyl]-triphenylphosphonium bromide (950 mg, 1.54 mmol, 1.00 equiv). The reaction mixture was stirred at 120° C., then (tert-butoxy)potassium (689 mg, 6.14 mmol, 4.00 equiv), in two portions for 1.5 hours. The reaction mixture was cooled to room temperature. The resulting mixture was concentrated under vacuum. The residue was applied onto a silica gel column with ethyl acetate/petroleum ether (1:25-1:15). This resulted in 90 mg (23%) of 5-bromo-6-chloro-2-ethyl-1H-indole as a light yellow solid.

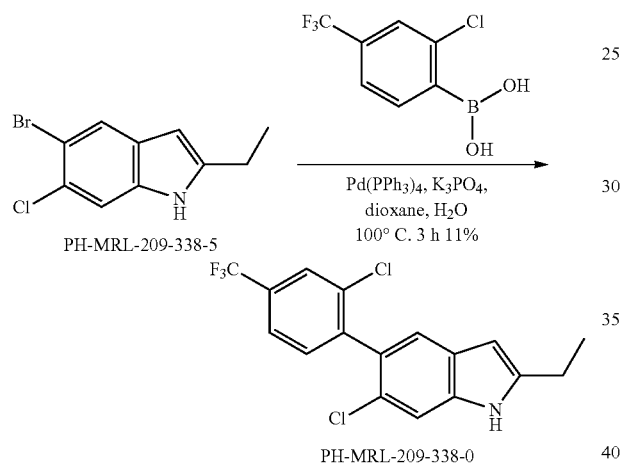

Finally, into a 50-mL round-bottom flask purged and maintained with an inert atmosphere of nitrogen, was placed dioxane (10 mL), water (2 mL), 5-bromo-6-chloro-2-ethyl-1H-indole (70 mg, 0.27 mmol, 1.00 equiv), [2-chloro-4-(trifluoromethyl)phenyl]boronic acid (122 mg, 0.54 mmol, 2.00 equiv), K3PO4 (172 mg, 0.81 mmol, 3.00 equiv), Pd(PPh3)4 (31 mg, 0.03 mmol, 0.10 equiv). The resulting solution was stirred for 3 h at 100° C. in an oil bath. The reaction mixture was cooled. The resulting solution was diluted with 40 mL of ethyl acetate. The resulting mixture was washed with 3×10 mL of Brine. The mixture was dried over anhydrous sodium sulfate and concentrated under vacuum. The residue was dissolved in 5 mL of methanol. The crude product was purified by Prep-HPLC. This resulted in 10.8 mg (11%) of 6-chloro-5-[2-chloro-4-(trifluoromethyl)phenyl]-2-ethyl-1H-indole as a light brown solid. (ES, m/z): 356 [M−H]−

H-NMR-PH-MRL-209-338-0: (300 MHz, DMSO, ppm): δ 11.25 (s, 1H), 8.00 (s, 1H), 7.79 (d, J=8.1 Hz, 1H), 7.59 (d, J=7.2 Hz, 1H), 7.45 (s, 1H), 7.37 (s, 1H), 6.21 (s, 1H), 2.72~2.77 (m, 2H), 1.28 (t, J=7.5 Hz, 3H).

Compound number 339 (i.e., 6-chloro-5-[2-chloro-4-(trifluoromethyl)phenyl]-2-propyl-1H-indole) was made as follows.

First, into a 100-mL 3-necked round-bottom flask purged and maintained with an inert atmosphere of nitrogen, was placed tetrahydrofuran (60 mL), (2-amino-5-bromo-4-chlorophenyl)methanol (1.84 g, 7.78 mmol, 1.00 equiv), TEA (1.74 g, 17.20 mmol, 2.20 equiv). This was followed by the addition of butanoyl chloride (1.73 g, 16.24 mmol, 2.10 equiv) dropwise with stirring at 5° C. The resulting solution was stirred for 0.5 h at room temperature.

Then the reaction mixture was prepared for the next step.

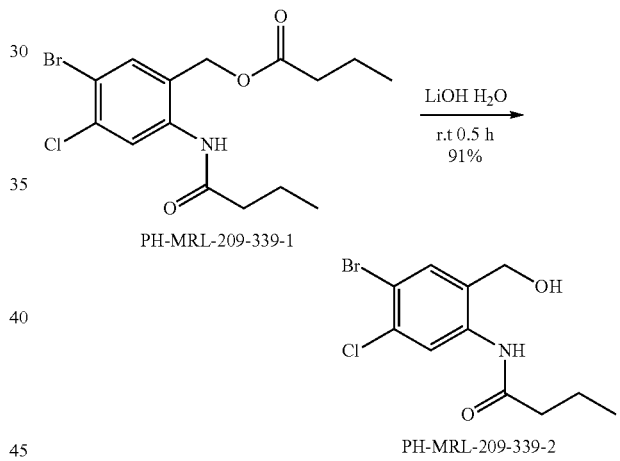

Next, 10% LiOH/H2O (40 mL) was added to the step one reaction mixture. The resulting solution was stirred for 0.5 hour at room temperature. The resulting solution was diluted with 100 mL of water. The resulting solution was extracted with 3×100 mL of ethyl acetate and the organic layers combined. The resulting mixture was washed with 3×80 mL of Brine. The organic phase was dried over anhydrous sodium sulfate and concentrated under vacuum. This resulted in 2.6 g (91%) of N-[4-bromo-5-chloro-2-(hydroxymethyl)phenyl]butanamide as a light yellow solid.

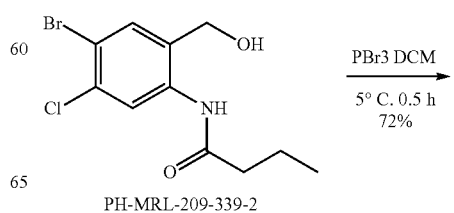

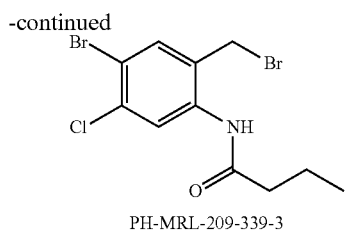

PH-MRL-209-339-3

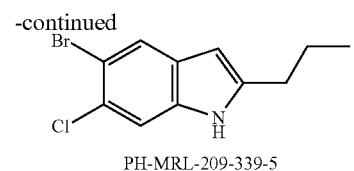

PH-MRL-209-339-5

Next, into a 100-mL 3-necked round-bottom flask purged and maintained with an inert atmosphere of nitrogen, was placed dichloromethane (40 mL), N-[4-bromo-5-chloro-2-(hydroxymethyl)phenyl]butanamide (1.5 g, 4.89 mmol, 1.00 equiv). This was followed by the addition of PBr₃ (520 mg, 1.92 mmol, 0.40 equiv) dropwise with stirring at 5° C. The resulting solution was stirred for 0.5 h at 5° C. The resulting solution was diluted with 50 mL of DCM. The reaction was then quenched by the addition of 1 mL of water. The resulting mixture was washed with 3×20 mL of Brine. The mixture was dried over anhydrous sodium sulfate and concentrated under vacuum. This resulted in 1.3 g (72%) of N-[4-bromo-2-(bromomethyl)-5-chlorophenyl]-butanamide as a white solid.

Next, into a 50-mL round-bottom flask purged and maintained with an inert atmosphere of nitrogen, was placed toluene (20 mL), [(5-bromo-2-butanamido-4-chlorophenyl)methyl]-triphenylphosphonium bromide (1.1 g, 1.74 mmol, 1.00 equiv), the reaction mixture was stirred at 120° C. in an oil bath, then added (tert-butoxy)potassium (780 mg, 6.95 mmol, 4.00 equiv) in two portions for 1.5 hours. The reaction mixture was cooled. The resulting mixture was concentrated under vacuum. The residue was applied onto a silica gel column with ethyl acetate/petroleum ether (1:25-1:20). This resulted in 100 mg (21%) of 5-bromo-6-chloro-2-propyl-1H-indole as a white solid.

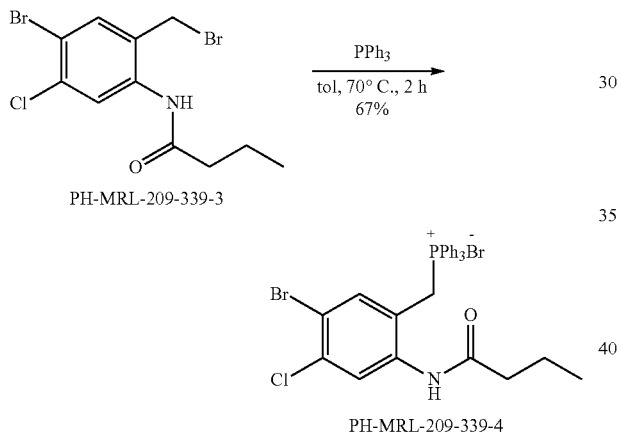

Finally, into a 50-mL round-bottom flask purged and maintained with an inert atmosphere of nitrogen, was placed dioxane (10 mL), water (2 mL), 5-bromo-6-chloro-2-propyl-1H-indole (70 mg, 0.26 mmol, 1.00 equiv), [2-chloro-4-(trifluoromethyl)phenyl]-boronic acid (115 mg, 0.51 mmol, 2.00 equiv), K₃PO₄ (163 mg, 0.77 mmol, 3.00 equiv), Pd(PPh₃)₄ (30 mg, 0.03 mmol, 0.10 equiv). The resulting solution was stirred for 3 h at 100° C. in an oil bath. The reaction mixture was cooled to room temperature. The resulting solution was diluted with 40 mL of ethyl acetate. The resulting mixture was washed with 3×10 mL of Brine. The organic phase was dried over anhydrous sodium sulfate and concentrated under vacuum. The residue was dissolved in 5 mL of methanol. The crude product was purified by Prep-HPLC. This resulted in 16 mg (17%) of 6-chloro-5-[2-chloro-4-(trifluoromethyl)-phenyl]-2-propyl-1H-indole as colorless oil. (ES, m/z): 370 [M–H]⁻

Next, into a 50-mL round-bottom flask purged and maintained with an inert atmosphere of nitrogen, was placed toluene (30 mL), N-[4-bromo-2-(bromomethyl)-5-chlorophenyl]butanamide (1 g, 2.71 mmol, 1.00 equiv), triphenylphosphine (780 mg, 2.97 mmol, 1.10 equiv). The resulting solution was stirred for 2 h at 70° C. in an oil bath. The reaction mixture was cooled to room temperature. The solids were collected by filtration, and the solid was washed with enough EtOAc. This resulted in 1.14 g (67%) of [(5-bromo-2-butanamido-4-chlorophenyl)methyl]-triphenylphosphonium bromide as a white solid.

H-NMR-PH-MRL-209-339-0: (300 MHz, DMSO, ppm): δ 11.23 (s, 1H), 7.98 (s, 1H), 7.78~7.80 (m, 1H), 7.59 (d, J=7.5 Hz, 1H), 7.45 (s, 1H), 7.37 (s, 1H), 6.22 (s, 1H), 2.70 (t, J=7.5 Hz, 2H), 1.68~1.75 (m, 2H), 0.95 (t, J=7.2 Hz, 3H).

Compound number 340 (i.e., 6-chloro-5-[2-chloro-4-(trifluoromethyl)phenyl]-2-(pentafluoroethyl)-1H-indole) was made as follows.

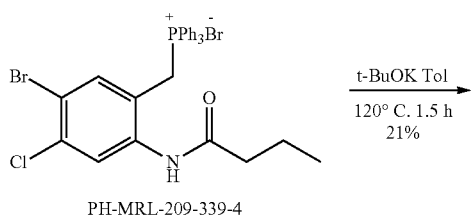

PH-MRL-209-339-4

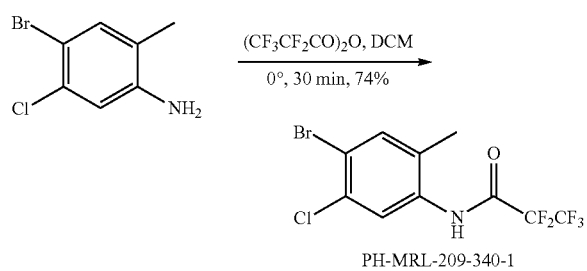

First, into a 100-mL 3-necked round-bottom flask, was placed 4-bromo-5-chloro-2-methylaniline (600 mg, 2.72 mmol, 1.00 equiv), dichloromethane (18 mL), pentafluoropropanoyl 2,2,3,3,3-pentafluoropropanoate (846 mg, 2.73 mmol, 1.00 equiv). The resulting solution was stirred for 30 min at 0° C. in a water/ice bath. The resulting mixture was concentrated under vacuum. This resulted in 740 mg (74%) of N-(4-bromo-5-chloro-2-methylphenyl)-2,2,3,3,3-pentafluoropropanamide as a light brown solid.

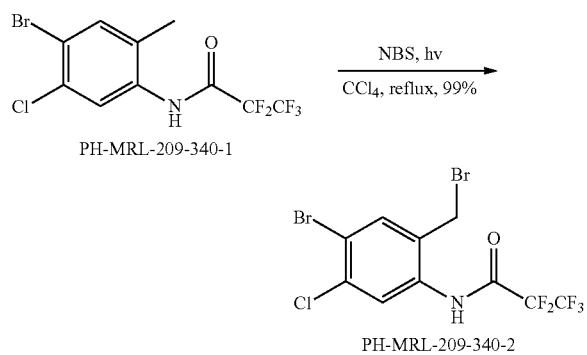

Next, into a 100-mL round-bottom flask, was placed N-(4-bromo-5-chloro-2-methylphenyl)-2,2,3,3,3-pentafluoropropanamide (400 mg, 1.09 mmol, 1.00 equiv), CCl₄ (10 mL), NBS (195.1 mg, 1.10 mmol, 1.00 equiv). The resulting solution was refluxed for 2 h under a 100 w incandescent bulb. The solids were filtered out. The resulting mixture was concentrated under vacuum. This resulted in 480 mg (99%) of N-[4-bromo-2-(bromomethyl)-5-chlorophenyl]-2,2,3,3,3-pentafluoropropanamide as a yellow solid.

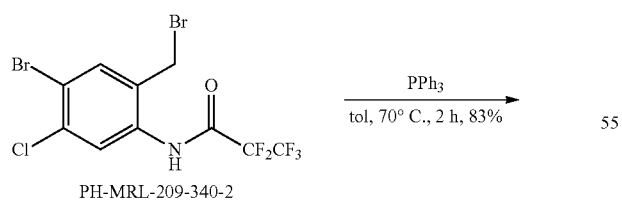

Next, into a 100-mL round-bottom flask, was placed N-[4-bromo-2-(bromomethyl)-5-chlorophenyl]-2,2,3,3,3-pentafluoropropanamide (470 mg, 1.06 mmol, 1.00 equiv), tooulene (10 mL), PPh₃ (334.4 mg, 1.27 mmol, 1.20 equiv). The resulting solution was stirred for 2 h at 70° C. in an oil bath. The resulting mixture was concentrated under vacuum. This resulted in 620 mg (83%) of [[5-bromo-4-chloro-2-(pentafluoropropanamido)phenyl]methyl]triphenylphosphonium bromide as a yellow solid.

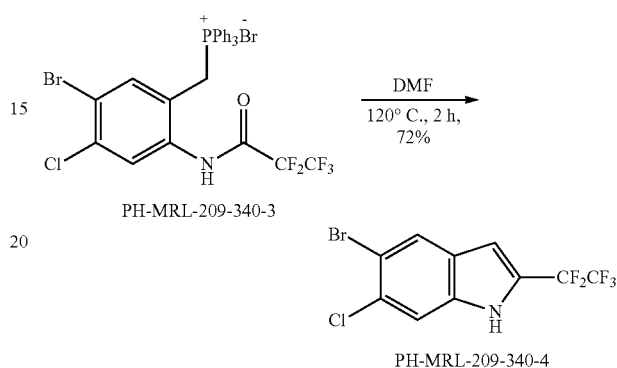

Next, into a 100-mL round-bottom flask, was placed [[5-bromo-4-chloro-2-(pentafluoropropanamido)phenyl]methyl]triphenylphosphonium bromide (450 mg, 0.64 mmol, 1.00 equiv), N,N-dimethylformamide (15 mL), TEA (321 mg, 3.17 mmol, 5.00 equiv). The resulting solution was stirred for 2 h at 120° C. in an oil bath. The resulting solution was diluted with 20 mL of H₂O. The resulting solution was extracted with 3×20 mL of ethyl acetate and the organic layers combined. The resulting mixture was washed with 3×20 mL of brine. The organic phase was dried over anhydrous sodium sulfate and concentrated under vacuum. This resulted in 160 mg (72%) of 5-bromo-6-chloro-2-(pentafluoroethyl)-1H-indole as brown oil.

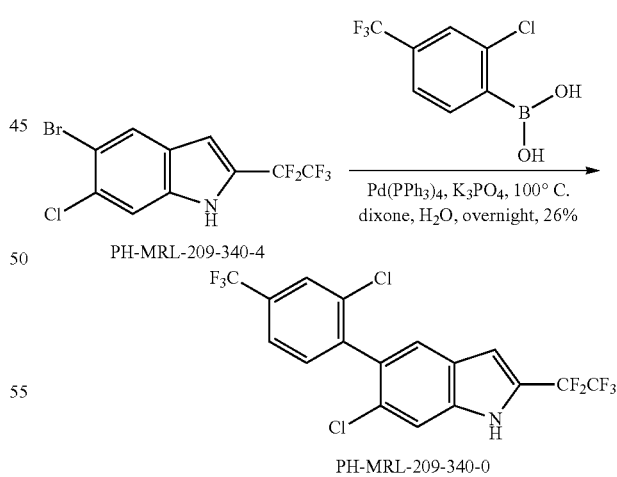

Finally, into a 50-mL round-bottom flask purged and maintained with an inert atmosphere of nitrogen, was placed 5-bromo-6-chloro-2-(pentafluoroethyl)-1H-indole (100 mg, 0.29 mmol, 1.00 equiv), dioxane (6 mL), water (1 mL), K₃PO₄ (183.3 mg, 0.86 mmol, 3.00 equiv), Pd(PPh₃)₄ (33.3 mg, 0.03 mmol, 0.10 equiv), [2-chloro-4-(trifluoromethyl)phenyl]boronic acid (130 mg, 0.58 mmol, 2.00 equiv). The resulting solution was stirred overnight at 100° C. in an oil bath. The resulting mixture was concentrated under vacuum. The residue was applied onto a silica gel column with ethyl acetate/petroleum ether (1:4). This resulted in 33 mg (26%) of 6-chloro-5-[2-chloro-4-(trifluoromethyl)phenyl]-2-(pentafluoroethyl)-1H-indole as a white solid. (ES, m/z): [M−H]⁻ 446; ¹H NMR (CDCl₃, 300 MHz) δ: 8.50 (s, 1H), 7.77 (s, 1H), 7.71-7.57 (m, 3H), 7.43 (d, J=9.0 Hz, 1H), 6.99 (s, 1H).

Compound number 341 (i.e., 6-chloro-5-[2-chloro-4-(trifluoromethyl)phenyl]-2-(heptafluoropropyl)-1H-indole) was made as follows.

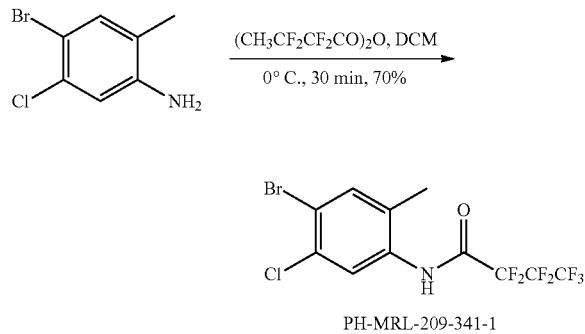

First, into a 50-mL 3-necked round-bottom flask, was placed 4-bromo-5-chloro-2-methylcyclohexan-1-amine (500 mg, 2.21 mmol, 1.00 equiv), dichloromethane (10 mL), heptafluorobutanoyl 2,2,3,3,4,4,4-heptafluorobutanoate (931.8 mg, 2.27 mmol, 1.00 equiv). The resulting solution was stirred for 30 min at 0° C. in a water/ice bath. The resulting mixture was concentrated under vacuum. This resulted in 640 mg (70%) of N-(4-bromo-5-chloro-2-methylphenyl)-2,2,3,3,4,4,4-heptafluorobutanamide as a brown solid.

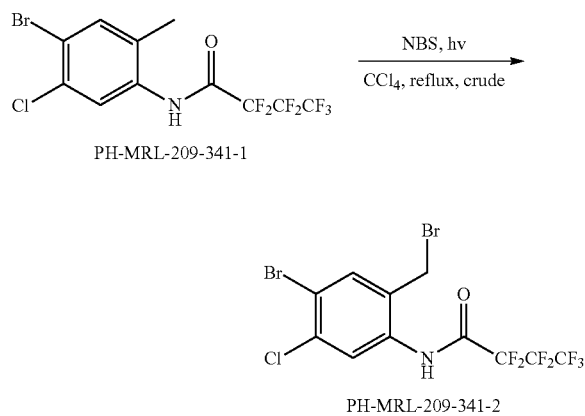

Next, into a 50-mL round-bottom flask, was placed N-(4-bromo-5-chloro-2-methylphenyl)-2,2,3,3,4,4,4-heptafluorobutanamide (400 mg, 0.96 mmol, 1.00 equiv), CCl₄ (10 mL), NBS (172 mg, 0.97 mmol, 1.00 equiv). The resulting solution was refluxed for 2 h under a 100 w incandescent bulb. The resulting mixture was concentrated under vacuum. This resulted in 520 mg (crude) of N-[4-bromo-2-(bromomethyl)-5-chlorophenyl]-2,2,3,3,4,4,4-heptafluorobutanamide as a brown solid.

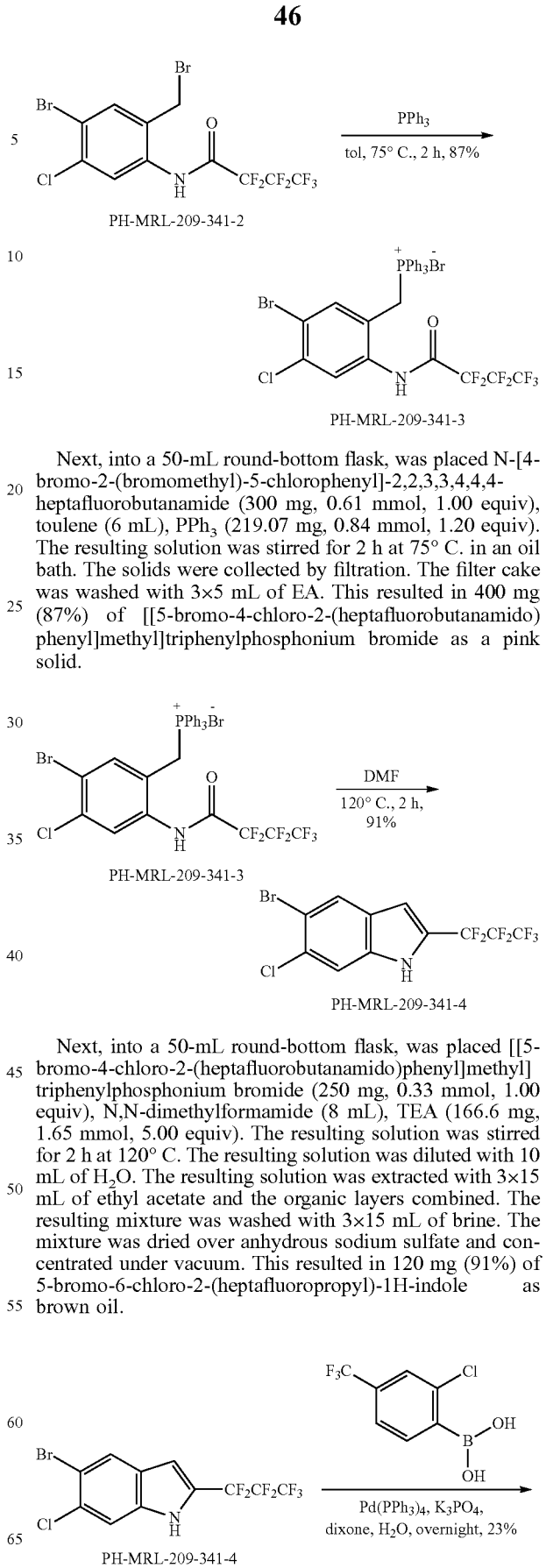

Next, into a 50-mL round-bottom flask, was placed N-[4-bromo-2-(bromomethyl)-5-chlorophenyl]-2,2,3,3,4,4,4-heptafluorobutanamide (300 mg, 0.61 mmol, 1.00 equiv), toulene (6 mL), PPh₃ (219.07 mg, 0.84 mmol, 1.20 equiv). The resulting solution was stirred for 2 h at 75° C. in an oil bath. The solids were collected by filtration. The filter cake was washed with 3×5 mL of EA. This resulted in 400 mg (87%) of [[5-bromo-4-chloro-2-(heptafluorobutanamido)phenyl]methyl]triphenylphosphonium bromide as a pink solid.

Next, into a 50-mL round-bottom flask, was placed [[5-bromo-4-chloro-2-(heptafluorobutanamido)phenyl]methyl]triphenylphosphonium bromide (250 mg, 0.33 mmol, 1.00 equiv), N,N-dimethylformamide (8 mL), TEA (166.6 mg, 1.65 mmol, 5.00 equiv). The resulting solution was stirred for 2 h at 120° C. The resulting solution was diluted with 10 mL of H₂O. The resulting solution was extracted with 3×15 mL of ethyl acetate and the organic layers combined. The resulting mixture was washed with 3×15 mL of brine. The mixture was dried over anhydrous sodium sulfate and concentrated under vacuum. This resulted in 120 mg (91%) of 5-bromo-6-chloro-2-(heptafluoropropyl)-1H-indole as brown oil.

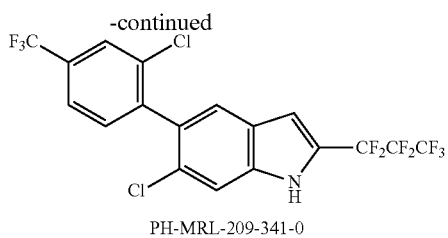

PH-MRL-209-341-0

Finally, into a 50-mL round-bottom flask, was placed 5-bromo-6-chloro-2-(heptafluoropropyl)-1H-indole (100 mg, 0.25 mmol, 1.00 equiv), dioxane (6 mL), water (1 mL), K$_3$PO$_4$ (160.2 mg, 0.75 mmol, 3.00 equiv), [2-chloro-4-(trifluoromethyl)phenyl]boronic acid (113.4 mg, 0.51 mmol, 2.00 equiv), Pd(PPh$_3$)$_4$ (29.1 mg, 0.03 mmol, 0.10 equiv). The resulting solution was stirred overnight at 100° C. in an oil bath. The resulting mixture was concentrated under vacuum. The residue was applied onto a silica gel column with ethyl acetate/petroleum ether (1:1). This resulted in 29.1 mg (23%) of 6-chloro-5-[2-chloro-4-(trifluoromethyl)phenyl]-2-(heptafluoropropyl)-1H-indole as a white solid. (ES, m/z): [M−H]$^-$ 496; $^1$H NMR (CDCl$_3$, 300 MHz) δ: 8.49 (s, 1H), 7.77 (s, 1H), 7.63-7.57 (m, 3H), 7.45-7.43 (m, 1H), 6.99 (s, 1H).

Compound number 342 (i.e., 6-chloro-5-[4-chloro-2-(trifluoromethyl)phenyl]-2-(trifluoromethyl)-1H-indole) was made as follows.

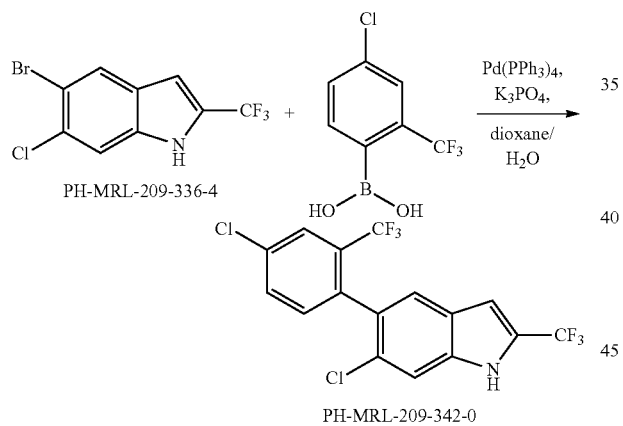

PH-MRL-209-336-4

PH-MRL-209-342-0

Into a 50-mL round-bottom flask, was placed a solution of 5-bromo-6-chloro-2-(trifluoromethyl)-1H-indole (80 mg, 0.27 mmol, 1.00 equiv) in dioxane/H$_2$O (1.8:0.3 mL), [4-chloro-2-(trifluoromethyl)phenyl]boronic acid (120 mg, 0.53 mmol, 2.00 equiv), Pd(PPh$_3$)$_4$ (31 mg, 0.03 mmol, 0.10 equiv), K$_3$PO$_4$ (171 mg, 3.00 equiv). The resulting solution was stirred overnight at 100° C. in an oil bath under N2 protection. The resulting mixture was concentrated under vacuum. The residue was applied onto a silica gel column with ethyl acetate/hexane (1:10). This resulted in 26.2 mg (25%) of 6-chloro-5-[4-chloro-2-(trifluoromethyl)phenyl]-2-(trifluoromethyl)-1H-indole as a white solid. (ES, m/z): [M−H]$^-$ 396.

$^1$H NMR (CDCl$_3$, 400 MHz) δ: 8.44 (s, 1H), 7.76-7.77 (m, 1H), 7.54-7.60 (m, 3H), 7.28 (s, 1H), 6.90-6.93 (m, 1H).

Compound number 343 (i.e., 6-chloro-5-(4-chlorophenyl)-2-(trifluoromethyl)-1H-indole) was made as follows.

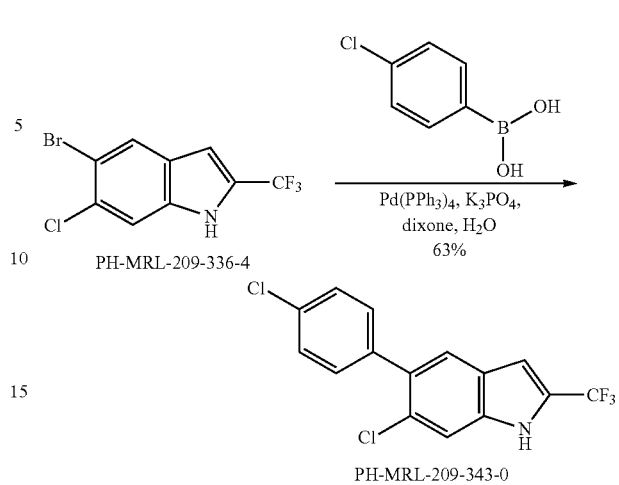

PH-MRL-209-336-4

PH-MRL-209-343-0

Into a 40-mL round-bottom flask purged and maintained with an inert atmosphere of nitrogen, was placed dioxane (10 mL), water (2 mL), 5-bromo-6-chloro-2-(trifluoromethyl)-1H-indole (80 mg, 0.27 mmol, 1.00 equiv), (4-chlorophenyl)boronic acid (84 mg, 0.54 mmol, 2.00 equiv), K3PO4 (170 mg, 0.80 mmol, 3.00 equiv), Pd(PPh3)4 (31 mg, 0.03 mmol, 0.10 equiv). The resulting solution was stirred overnight at 100° C. in an oil bath. The reaction mixture was cooled. The resulting solution was diluted with 50 mL of ethyl acetate. The resulting mixture was washed with 3×20 mL of brine. The resulting mixture was concentrated under vacuum. The residue was purified by preparative TLC (EtOAc:PE=1:20). This resulted in 14.1 mg (16%) of 6-chloro-5-(4-chlorophenyl)-2-(trifluoromethyl)-1H-indole as a white solid. (ES, m/z): 328[M−H]$^-$ H-NMR-PH-MRL-209-343-0: (300 MHz, DMSO, ppm): δ 12.55 (s, 1H), 7.72 (s, 1H), 7.65 (s, 1H), 7.51~7.54 (m, 2H), 7.44~7.47 (m, 2H), 7.10 (s, 1H).

Compound number 344 (i.e., 6-chloro-5-(4-fluorophenyl)-2-(trifluoromethyl)-1H-indole) was made as follows.

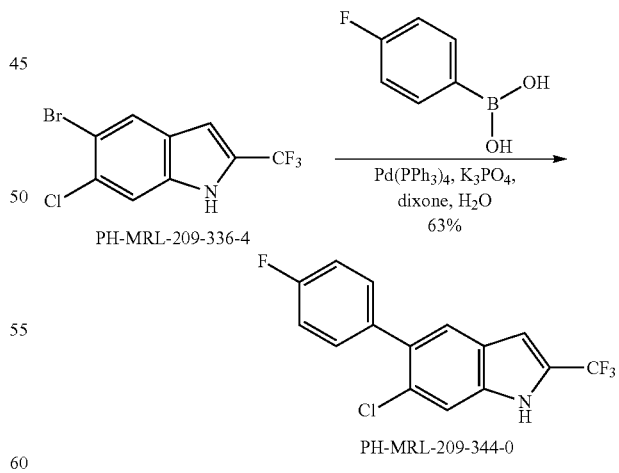

PH-MRL-209-336-4

PH-MRL-209-344-0

Into a 40-mL round-bottom flask purged and maintained with an inert atmosphere of nitrogen, was placed dioxane (10 mL), water (2 mL), 5-bromo-6-chloro-2-(trifluoromethyl)-1H-indole (80 mg, 0.27 mmol, 1.00 equiv), (4-fluorophenyl)boronic acid (75 mg, 0.54 mmol, 2.00 equiv), K$_3$PO$_4$ (170 mg, 0.80 mmol, 3.00 equiv), Pd(PPh$_3$)$_4$ (31 mg, 0.03 mmol, 0.10 equiv). The resulting solution was stirred overnight at 100° C. in an oil bath. The reaction mixture was cooled. The resulting solution was diluted with 50 mL of ethyl acetate. The resulting mixture was washed with 3×20 mL of brine. The organic phase was concentrated under vacuum. The residue was purified by preparative TLC (EtOAc:PE=1:20). This resulted in 41.5 mg (49%) of 6-chloro-5-(4-fluorophenyl)-2-(trifluoromethyl)-1H-indole as a white solid. (ES, m/z): 312[M−H]$^-$ H-NMR-PH-MRL-209-344-0: (300 MHz, DMSO, ppm): δ 12.51 (s, 1H), 7.70 (s, 1H), 7.64 (s, 1H), 7.45~7.49 (m, 2H), 7.29 (t, J=9.0 Hz, 2H), 7.09 (s, 1H).

Compound number 345 (i.e., 6-chloro-2-(trifluoromethyl)-5-[4-(trifluoromethyl)phenyl]-1H-indole) was made as follows.

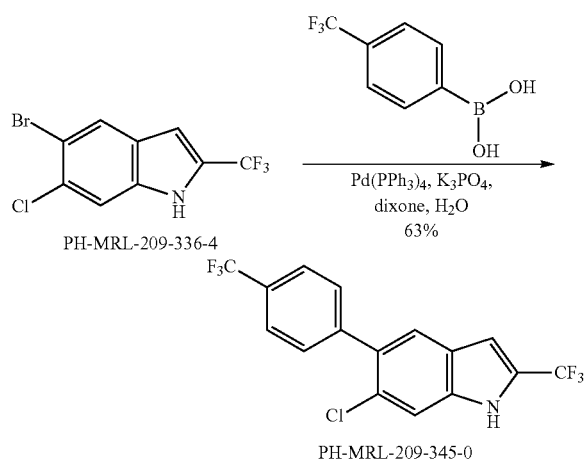

Into a 40-mL round-bottom flask purged and maintained with an inert atmosphere of nitrogen, was placed dioxane (10 mL), water (2 mL), 5-bromo-6-chloro-2-(trifluoromethyl)-1H-indole (80 mg, 0.27 mmol, 1.00 equiv), [4-(trifluoromethyl)phenyl]boronic acid (101 mg, 0.53 mmol, 2.00 equiv), K$_3$PO4 (170 mg, 0.80 mmol, 3.00 equiv), Pd(PPh$_3$)$_4$ (31 mg, 0.03 mmol, 0.10 equiv). The resulting solution was stirred overnight at 100° C. in an oil bath. The reaction mixture was cooled. The resulting solution was diluted with 50 mL of ethyl acetate. The resulting mixture was washed with 3×20 mL of brine. The resulting mixture was concentrated under vacuum. The residue was purified by preparative TLC (EtOAc:PE=1:20). This resulted in 67 mg (69%) of 6-chloro-2-(trifluoromethyl)-5-[4-(trifluoromethyl)phenyl]-1H-indole as a white solid. (ES, m/z): 362[M−H]$^-$ H-NMR-PH-MRL-209-345-0: (300 MHz, DMSO, ppm): δ 12.59 (s, 1H), 7.81~7.84 (m, 2H), 7.77 (s, 1H), 7.66~7.69 (m, 3H), 7.12 (s, 1H).

Compound number 346 (i.e., 6-chloro-5-(2-chlorophenyl)-2-(trifluoromethyl)-1H-indole) was made as follows.

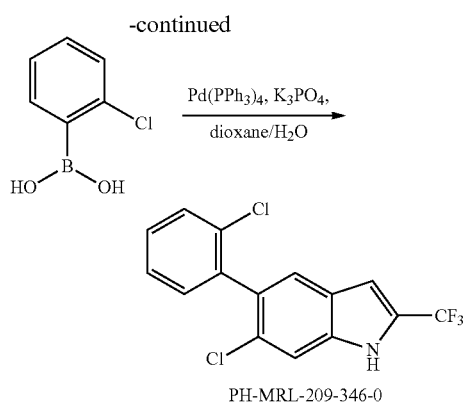

Into a 50-mL round-bottom flask, was placed a solution of 5-bromo-6-chloro-2-(trifluoromethyl)-1H-indole (80 mg, 0.27 mmol, 1.00 equiv) in dioxane/H$_2$O (1.8:0.3 mL), (2-chlorophenyl)boronic acid (84 mg, 0.54 mmol, 2.00 equiv), Pd(PPh$_3$)$_4$ (31 mg, 0.03 mmol, 0.10 equiv), K$_3$PO$_4$ (171 mg, 3.00 equiv). The resulting solution was stirred overnight at 100° C. in an oil bath. The resulting mixture was concentrated under vacuum. The residue was applied onto a silica gel column with ethyl acetate/hexane (1:10). This resulted in 20 mg (23%) of 6-chloro-5-(2-chlorophenyl)-2-(trifluoromethyl)-1H-indole as colorless oil. (ES, m/z): [M−H]$^-$ 328. $^1$H NMR (CDCl$_3$, 400 MHz) δ: 8.45 (s, 1H), 7.59-7.60 (m, 2H), 7.53-7.49 (s, 1H), 7.30-7.40 (m, 3H), 6.96 (s, 1H).

Compound number 347 (i.e., 6-chloro-5-(3-chlorophenyl)-2-(trifluoromethyl)-1H-indole) was made as follows.

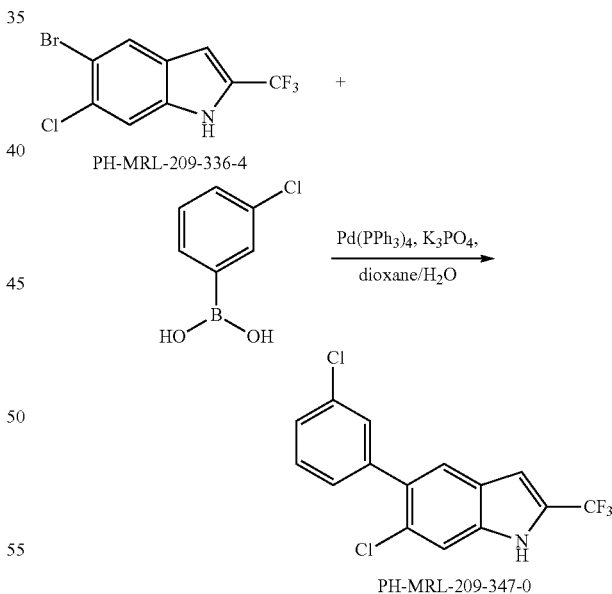

Into a 50-mL round-bottom flask, was placed a solution of 5-bromo-6-chloro-2-(trifluoromethyl)-1H-indole (80 mg, 0.27 mmol, 1.00 equiv) in dioxane/H$_2$O (1.8:0.3 mL), (3-chlorophenyl)boronic acid (84 mg, 0.54 mmol, 2.00 equiv), Pd(PPh$_3$)$_4$ (31 mg, 0.03 mmol, 0.10 equiv), K$_3$PO$_4$ (171 mg, 3.00 equiv). The resulting solution was stirred overnight at 100° C. in an oil bath under N$_2$ protection. The solid was dried in an oven under reduced pressure. The residue was applied onto a silica gel column with ethyl acetate/hexane (1:10). This resulted in 12.6 mg (14%) of 6-chloro-5-(3-chlorophenyl)-2-(trifluoromethyl)-1H-indole as a light brown solid. (ES, m/z): [M−H]⁻ 328. ¹H NMR (CDCl₃, 400 MHz) δ: 8.44 (s, 1H), 7.56-7.61 (m, 2H), 7.44 (s, 1H), 7.35 (s, 3H), 6.92 (s, 1H).

Compound number 348 (i.e., 6-chloro-5-(3,4-dichlorophenyl)-2-(trifluoromethyl)-1H-indole) was made as follows.

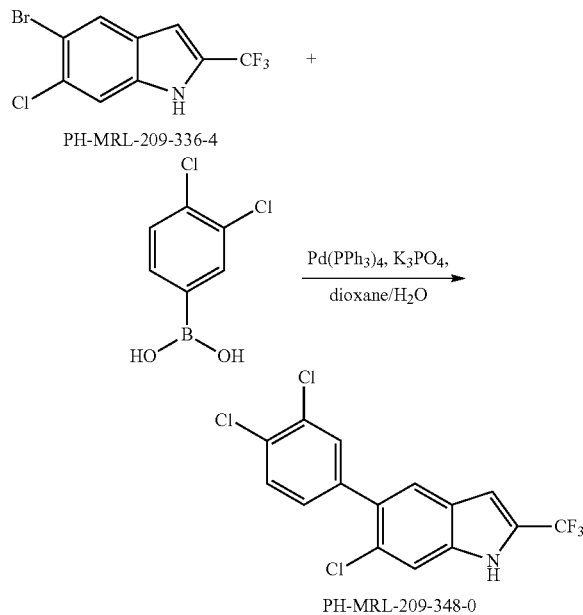

Into a 50-mL round-bottom flask, was placed a solution of 5-bromo-6-chloro-2-(trifluoromethyl)-1H-indole (80 mg, 0.27 mmol, 1.00 equiv) in dioxane/H₂O (1.8:0.3 mL), (3,4-dichlorophenyl)boronic acid (102 mg, 0.53 mmol, 2.00 equiv), Pd(PPh₃)₄ (31 mg, 0.03 mmol, 0.10 equiv), K₃PO₄ (171 mg, 3.00 equiv). The resulting solution was stirred overnight at 100° C. in an oil bath under N₂ protection. The resulting mixture was concentrated under vacuum. The residue was applied onto a silica gel column with ethyl acetate/hexane (1:10). This resulted in 38.7 mg (40%) of 6-chloro-5-(3,4-dichlorophenyl)-2-(trifluoromethyl)-1H-indole as a white solid. (ES, m/z): [M−H]⁻ 362. ¹H NMR (CDCl₃, 400 MHz) δ: 8.42 (s, 1H), 7.49-7.60 (m, 4H), 7.28-7.31 (m, 1H), 6.93 (s, 1H).

Compound number 349 (i.e., 6-chloro-5-(pyridin-4-yl)-2-(trifluoromethyl)-1H-indole) was made as follows.

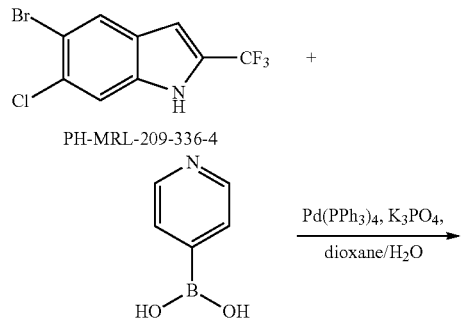

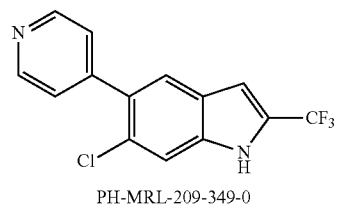

Into a 50-mL round-bottom flask, was placed a solution of 5-bromo-6-chloro-2-(trifluoromethyl)-1H-indole (80 mg, 0.27 mmol, 1.00 equiv) in dioxane/H₂O (1.8:0.3 mL), (pyridin-4-yl)boronic acid (66 mg, 0.54 mmol, 2.00 equiv), Pd(PPh₃)₄ (31 mg, 0.03 mmol, 0.10 equiv), K₃PO₄ (171 mg, 0.81 mmol, 3.00 equiv). The resulting solution was stirred overnight at 100° C. in an oil bath under N₂ protection. The resulting mixture was concentrated under vacuum. The residue was applied onto a silica gel column with ethyl acetate/hexane (1:10). This resulted in 24.2 mg (30%) of 6-chloro-5-(pyridin-4-yl)-2-(trifluoromethyl)-1H-indole as a white solid. (ES, m/z): [M−H]⁻ 295. ¹H NMR (CDCl₃, 400 MHz) δ: 12.62 (s, 1H), 8.64-8.66 (m, 2H), 7.79 (s, 1H), 7.68 (s, 1H), 7.48-7.50 (m, 2H), 7.12 (s, 1H).

Compound number 350 (i.e., 6-chloro-5-(4-chlorophenoxy)-2-(trifluoromethyl)-1H-indole was made as follows.

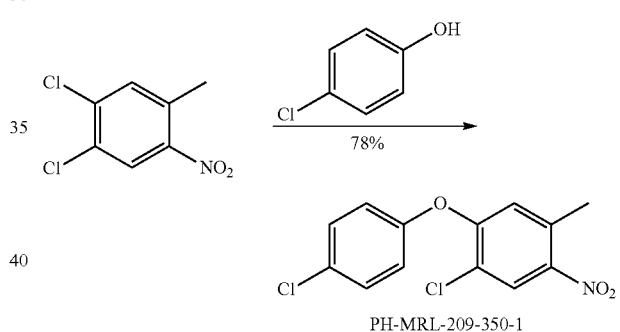

First, into a 80-mL round-bottom flask, was placed 1,2-dichloro-4-methyl-5-nitrobenzene (1 g, 4.9 mmol, 1.00 equiv), N,N-dimethylformamide (20 mL), potassium carbonate (2 g, 14.5 mmol, 3.00 equiv), 4-chlorophenol (0.62 g, 4.8 mmol, 1.00 equiv). The resulting solution was stirred for 2 h at 120° C. in an oil bath. The resulting solution was diluted with 20 mL of H₂O. The resulting solution was extracted with 3×20 mL of ethyl acetate and the organic layers combined. The resulting mixture was washed with 3×20 mL of brine. The organic phase was dried over anhydrous sodium sulfate and concentrated under vacuum. This resulted in 1.2 g (78%) of 1-chloro-2-(4-chlorophenoxy)-4-methyl-5-nitrobenzene as a black solid.

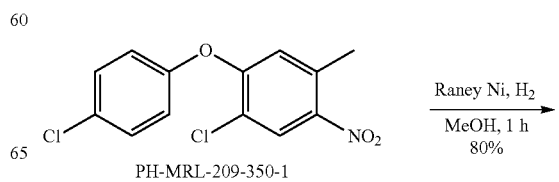

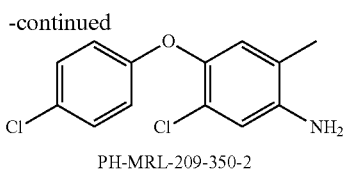
PH-MRL-209-350-2

Next, into a 100-mL round-bottom flask, was placed methanol (40 mL), Raney Ni (200 mg), 1-chloro-2-(4-chlorophenoxy)-4-methyl-5-nitrobenzene (1.1 g, 3.69 mmol, 1.00 equiv). The flask was evacuated and flushed three times with hydrogen. The mixture was stirred 1 h at room temperature under an atmosphere of hydrogen. The solids were filtered out. The resulting mixture was concentrated under vacuum. This resulted in 800 mg (81%) of 5-chloro-4-(4-chlorophenoxy)-2-methylaniline as a black solid.

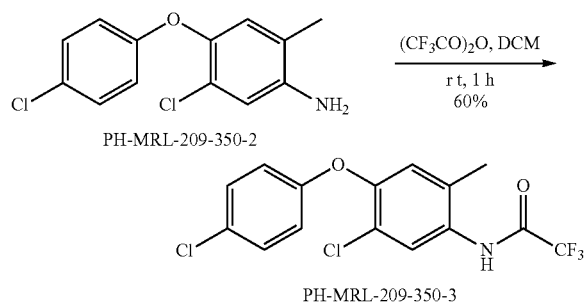

Next, into a 100-mL 3-necked round-bottom flask purged and maintained with an inert atmosphere of nitrogen, was placed dichloromethane (40 mL), 5-chloro-4-(4-chlorophenoxy)-2-methylaniline (800 mg, 2.98 mmol, 1.00 equiv). This was followed by the addition of TFAA (752 mg, 3.58 mmol, 1.20 equiv) dropwise with stirring at 0° C. The resulting solution was stirred for 1 h at room temperature. The resulting mixture was concentrated under vacuum. This resulted in 600 mg (55%) of N-[5-chloro-4-(4-chlorophenoxy)-2-methylphenyl]-2,2,2-trifluoroacetamide as a red solid.

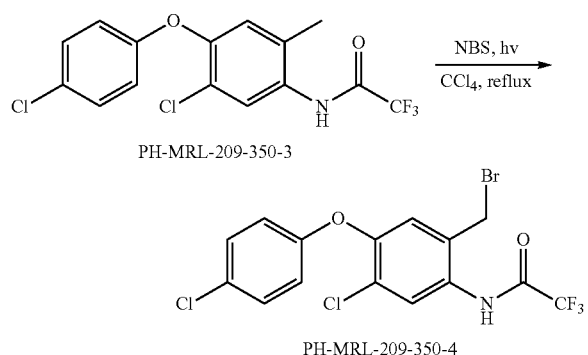

Next, into a 50-mL round-bottom flask purged and maintained with an inert atmosphere of nitrogen, was placed tetrachloromethane (20 mL), N-[5-chloro-4-(4-chlorophenoxy)-2-methylphenyl]-2,2,2-trifluoroacetamide (600 mg, 1.65 mmol, 1.00 equiv), boranylidene(sulfanyl)amine (288 mg, 4.89 mmol, 0.98 equiv). The resulting solution was stirred for 3 h at 80° C. by the infrared light and initiated by light. The reaction mixture was cooled. The solids were filtered out, and washed with enough CCl₄. Then the filtrate was concentrated under vacuum. This resulted in 500 mg (crude) of N-[2-(bromomethyl)-5-chloro-4-(4-chlorophenoxyl)phenyl]-2,2,2-trifluoroacetamide as a brown solid.

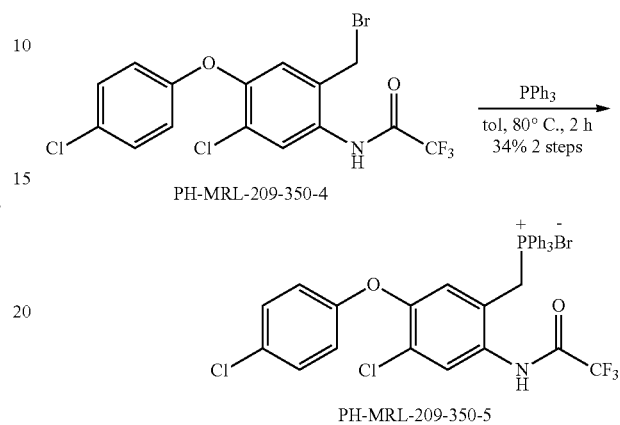

Next, into a 50-mL round-bottom flask purged and maintained with an inert atmosphere of nitrogen, was placed toluene (30 mL), N-[2-(bromomethyl)-5-chloro-4-(4-chlorophenoxyl)phenyl]-2,2,2-trifluoroacetamide (500 mg, 1.13 mmol, 1.00 equiv), triphenylphosphine (354 mg, 1.35 mmol, 1.20 equiv). The resulting solution was stirred for 2 h at 80° C. in an oil bath. The reaction mixture was cooled. The solids were filtered out and washed with enough EtOAc. The solid was dried under infrared light. This resulted in 400 mg (50%) of N-[2-[(bromotriphenyl-ˆ[5]-phosphanyl)methyl]-5-chloro-4-(4-chlorophenoxyl)phenyl]-2,2,2-trifluoroacetamide as a white solid.

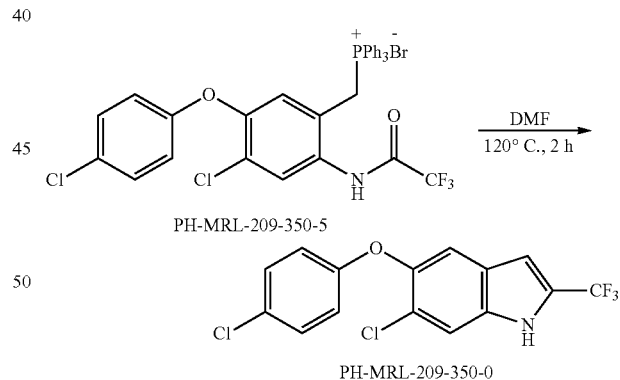

Finally, into a 40-mL round-bottom flask, was placed N,N-dimethylformamide (10 mL), [[4-chloro-5-(4-chlorophenoxy)-2-(trifluoroacetamido)phenyl]methyl]triphenylphosphonium bromide (150 mg, 0.21 mmol, 1.00 equiv), TEA (107 mg, 1.06 mmol, 5.00 equiv). The resulting solution was stirred for 2 h at 120° C. in an oil bath. The reaction mixture was cooled. The resulting solution was poured into 50 mL of water/ice. The resulting solution was extracted with 3×30 mL of ethyl acetate and the organic layers combined. The resulting mixture was washed with 3×15 mL of brine. The resulting mixture was concentrated under vacuum. The residue was purified by preparative TLC (EtOAc:PE=1:20). This resulted in 41 mg (56%) of 6-chloro-5-(4-chlorophenoxy)-2-(trifluoromethyl)-1H-indole as a white solid. (ES, m/z): 344[M−H]⁻

H-NMR-PH-MRL-209-350-0: (300 MHz, DMSO, ppm): δ 12.56 (s, 1H), 7.69 (s, 1H), 7.57 (s, 1H), 7.36~7.41 (m, 2H), 7.05 (s, 1H), 6.88~6.93 (m, 2H).

Compound number 351 (i.e., 6-chloro-5-(2-chlorophenoxy)-2-(trifluoromethyl)-1H-indole) was made as follows.

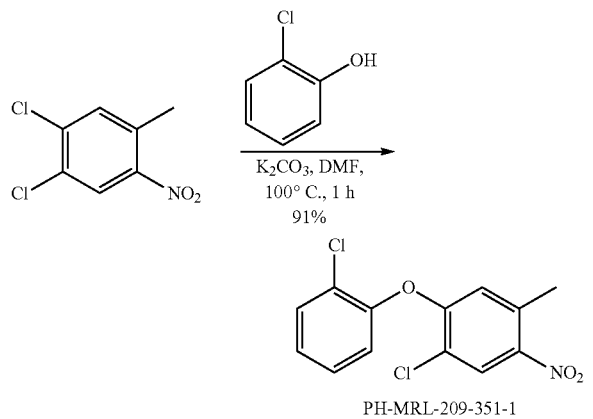

First, into a 100-mL round-bottom flask, was placed 1,2-dichloro-4-methyl-5-nitrobenzene (1 g, 4.85 mmol, 1.00 equiv), N,N-dimethylformamide (20 g, 273.64 mmol, 56.38 equiv), potassium carbonate (2 g, 14.47 mmol, 3.00 equiv), 2-chlorophenol (621 mg, 4.83 mmol, 1.00 equiv). The resulting solution was stirred for 1 h at 100° C. in an oil bath. The resulting solution was diluted with 20 mL of H₂O. The resulting solution was extracted with 3×20 mL of ethyl acetate and the organic layers combined. The resulting mixture was washed with 3×20 mL of brine. The mixture was dried over anhydrous sodium sulfate and concentrated under vacuum. This resulted in 1.24 g (91%) of 1-chloro-2-(2-chlorophenyl)-4-methyl-5-nitrobenzene as a brown solid.

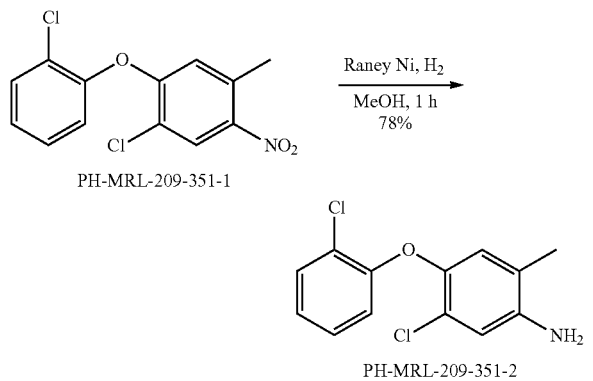

Next, into a 100-mL round-bottom flask, was placed methanol (30 mL), Raney Ni (200 mg, 20% W/W equiv), 1-chloro-2-(2-chlorophenoxy)-4-methyl-5-nitrobenzene (1 g, 3.35 mmol, 1.00 equiv), hydrogen (g, enough). The resulting solution was stirred for 1 h at room temperature. The solids were filtered out. The resulting mixture was concentrated under vacuum. This resulted in 700 mg (78%) of 5-chloro-4-(2-chlorophenoxy)-2-methylaniline as a brown solid.

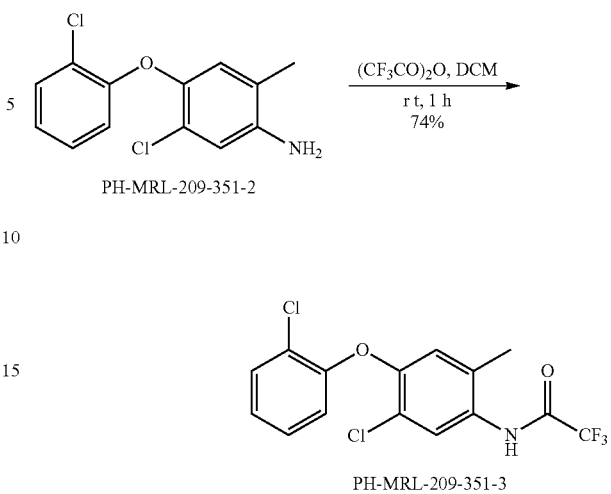

Next, into a 100-mL 3-necked round-bottom flask, was placed dichloromethane (30 mL), 5-chloro-4-(2-chlorophenoxy)-2-methylaniline (700 mg, 2.61 mmol, 1.00 equiv), This was followed by the addition of TFAA (658 mg, 3.13 mmol, 1.20 equiv) dropwise with stirring at 0° C. The resulting solution was stirred for 1 h at room temperature. The resulting mixture was concentrated under vacuum. This resulted in 700 mg (74%) of N-[5-chloro-4-(2-chlorophenoxy)-2-methylphenyl]-2,2,2-trifluoroacetamide as a brown solid.

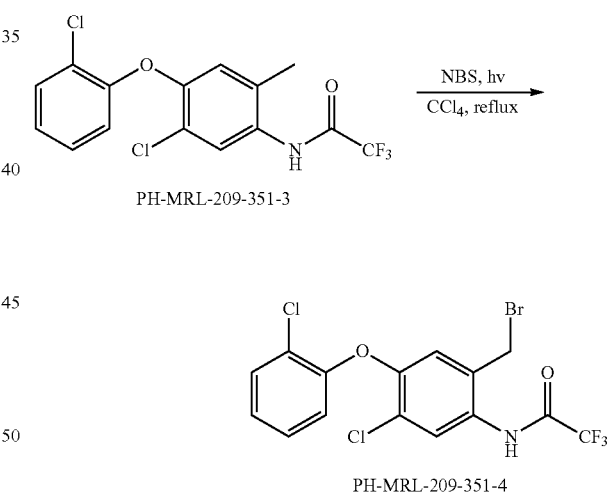

Next, into a 50-mL round-bottom flask purged and maintained with an inert atmosphere of nitrogen, was placed tetrachloromethane (30 mL), NBS (335 mg, 1.88 mmol, 0.98 equiv), N-[5-chloro-4-(2-chlorophenoxy)-2-methylphenyl]-2,2,2-trifluoroacetamide (700 mg, 1.92 mmol, 1.00 equiv). The resulting solution was stirred for 4 h at 80° C. by infrared light and initiated by light. The reaction mixture was cooled to room temperature. The solids were filtered out and washed with enough CCl₄. The filtrate was concentrated under vacuum. This resulted in 500 mg (crude) of N-[2-(bromomethyl)-5-chloro-4-(2-chlorophenoxyl)phenyl]-2,2,2-trifluoroacetamide as a light brown solid. The product was used in the next step directly without further purification.

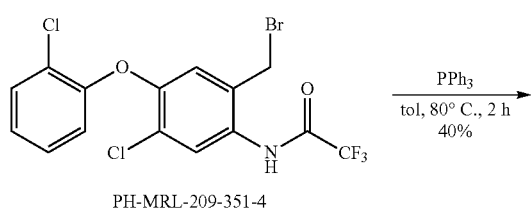

PH-MRL-209-351-4

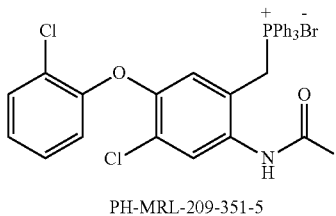

PH-MRL-209-351-5

Next, into a 50-mL round-bottom flask purged and maintained with an inert atmosphere of nitrogen, was placed toluene (30 mL), N-[2-(bromomethyl)-5-chloro-4-(2-chlorophenoxyl)phenyl]-2,2,2-trifluoroacetamide (500 mg, 1.13 mmol, 1.00 equiv), triphenylphosphine (603 mg, 2.30 mmol, 1.20 equiv). The resulting solution was stirred for 2 h at 80° C. in an oil bath. The reaction mixture was cooled to room temperature. The solids were collected by filtration. The solid was dried in an oven under reduced pressure. This resulted in 320 mg (40%) of [[4-chloro-5-(2-chlorophenoxy)-2-(trifluoroacetamido)phenyl]methyl]triphenylphosphonium bromide as a white solid.

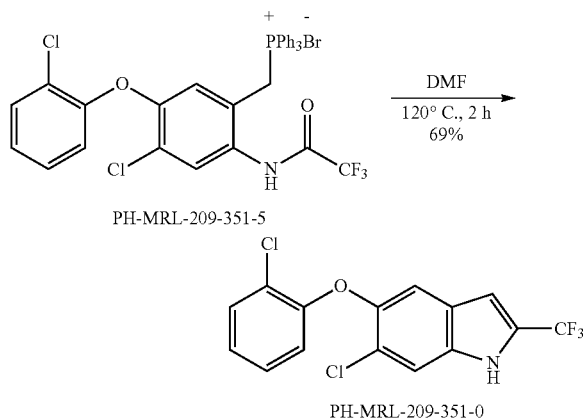

PH-MRL-209-351-5

PH-MRL-209-351-0

Finally, into a 40-mL round-bottom flask purged and maintained with an inert atmosphere of nitrogen, was placed N,N-dimethylformamide (10 mL), [[4-chloro-5-(2-chlorophenoxy)-2-(trifluoroacetamido)phenyl]methyl]triphenyl-phosphonium bromide (150 mg, 0.21 mmol, 1.00 equiv), TEA (107 mg, 1.06 mmol, 5.00 equiv). The resulting solution was stirred for 2 h at 120° C. in an oil bath. The reaction mixture was cooled to room temperature. The resulting solution was diluted with 1×50 mL of H$_2$O. The resulting solution was extracted with 3×30 mL of ethyl acetate and the organic layers combined. The resulting mixture was washed with 3×15 ml, of brine. The resulting organic phase was concentrated under vacuum. The residue was purified by prep-HPLC. This resulted in 51 mg (69%) of 6-chloro-5-(2-chlorophenoxy)-2-(trifluoromethyl)-1H-indole as a light brown solid. (ES, m/z): 344[M−H]$^−$ H-NMR-PH-MRL-209-351-0: (300 MHz, DMSO, ppm): δ 12.51 (brs, 1H), 7.70 (s, 1H), 7.59 (dd, J=1.5, 9.0 Hz, 1H), 7.44 (s, 1H), 7.28 (dt, J=3.0, 9.0 Hz, 1H), 7.14 (dt, J=1.5, 7.8 Hz, 1H), 7.03 (s, 1H), 6.78 (dd, J=1.5, 8.4 Hz, 1H).

Compound number 352 (i.e., 6-chloro-2-(trifluoromethyl)-5-[4-(trifluoromethyl)phenoxy]-1H-indole) was made as follows.

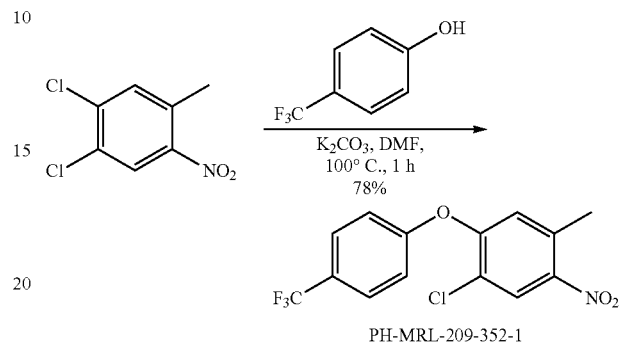

PH-MRL-209-352-1

First, into a 100-mL round-bottom flask, was placed 1,2-dichloro-4-methyl-5-nitrobenzene (1 g, 4.85 mmol, 1.00 equiv), N,N-dimethylformamide (20 mL), potassium carbonate (2 g, 14.47 mmol, 3.00 equiv), 4-(trifluoromethyl) phenol (786 mg, 4.85 mmol, 1.00 equiv). The resulting solution was stirred for 2 h at 100° C. in an oil bath. The resulting solution was diluted with 20 mL of H$_2$O. The resulting solution was extracted with 3×20 mL of ethyl acetate and the organic layers combined. The resulting mixture was washed with 3×20 mL of brine. The organic phase was dried over anhydrous sodium sulfate and concentrated under vacuum. This resulted in 1.2 g (78%) of 1-chloro-4-methyl-5-nitro-2-[4-(trifluoromethyl)phenyl] benzene as a brown solid.

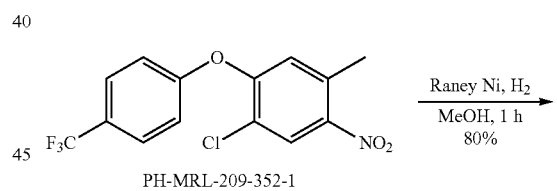

PH-MRL-209-352-1

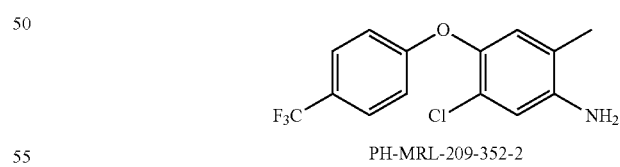

PH-MRL-209-352-2

Next, into a 100-mL round-bottom flask, was placed methanol (30 mL), Raney Ni (200 mg), 1-chloro-4-methyl-5-nitro-2-[4-(trifluoromethyl)phenoxy]benzene (1.1 g, 3.32 mmol, 1.00 equiv). The flask was evacuated and flushed three times with hydrogen. The mixture was stirred 1 h at room temperature under an atmosphere of hydrogen. The solids were filtered out. The resulting mixture was concentrated under vacuum. This resulted in 800 mg (80%) of 5-chloro-2-methyl-4-[4-(trifluoromethyl)phenoxy]aniline as a brown solid.

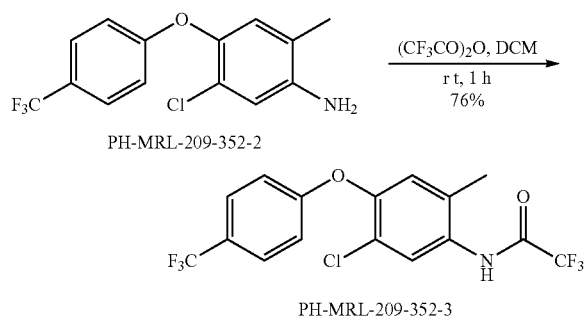

PH-MRL-209-352-2

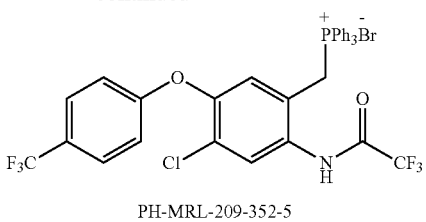

PH-MRL-209-352-5

Next, into a 100-mL 3-necked round-bottom flask purged and maintained with an inert atmosphere of nitrogen, was placed dichloromethane (30 mL), 5-chloro-2-methyl-4-[4-(trifluoromethyl)phenoxy]aniline (800 mg, 2.65 mmol, 1.00 equiv). This was followed by the addition of TFAA (670 mg, 3.19 mmol, 1.20 equiv) dropwise with stirring at 0° C. The resulting solution was stirred for 1 h at room temperature. The resulting mixture was concentrated under vacuum. This resulted in 800 mg (76%) of N-[5-chloro-2-methyl-4-[4-(trifluoromethyl)phenoxy]phenyl]-2,2,2-trifluoroacetamide as a brown solid.

Next, into a 50-mL round-bottom flask purged and maintained with an inert atmosphere of nitrogen, was placed toluene (30 mL), N-[2-(bromomethyl)-5-chloro-4-[4-(trifluoromethyl)phenoxy]phenyl]-2,2,2-trifluoroacetamide (600 mg, 1.26 mmol, 1.00 equiv), triphenylphosphine (628 mg, 2.39 mmol, 1.20 equiv). The resulting solution was stirred for 2 h at 80° C. in an oil bath. The reaction mixture was cooled to room temperature. The solids were collected by filtration and washed with EtOAc. The solid was dried under infrared light. This resulted in 700 mg (75%) of [[4-chloro-2-(trifluoroacetamido)-5-[4-(trifluoromethyl)phenoxy]phenyl]methyl]triphenylphosphonium bromide as a white solid.

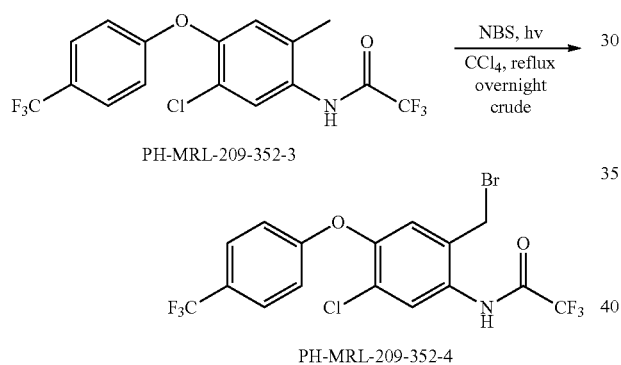

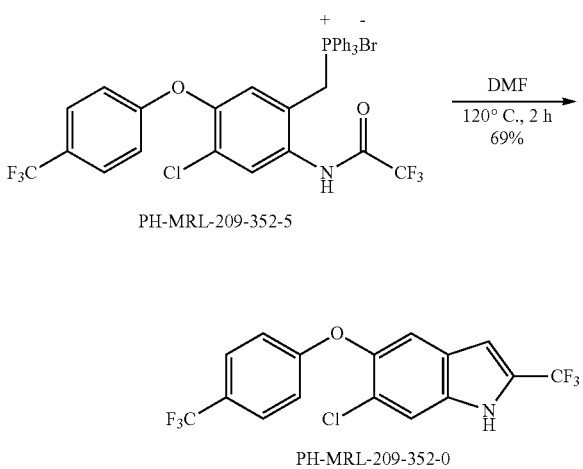

Next, into a 50-mL round-bottom flask purged and maintained with an inert atmosphere of nitrogen, was placed tetrachloromethane (30 mL), N-[5-chloro-2-methyl-4-[4-(trifluoromethyl)phenoxy]phenyl]-2,2,2-trifluoroacetamide (800 mg, 2.01 mmol, 1.00 equiv), NBS (430 mg, 7.30 mmol, 0.98 equiv). The resulting solution was stirred for 2 days at 80° C. by infrared light and initiated by light. The reaction mixture was cooled. The solids were filtered out and washed with enough CCl₄. The filtrate was concentrated under vacuum. This resulted in 600 mg (crude) of N-[2-(bromomethyl)-5-chloro-4-[4-(trifluoromethyl)phenoxy]phenyl]-2,2,2-trifluoroacetamide as a light brown solid.

Finally, into a 40-mL round-bottom flask, was placed N,N-dimethylformamide (10 mL), [[4-chloro-2-(trifluoroacetamido)-5-[4-(trifluoromethyl)phenoxy]phenyl]methyl]triphenylphosphanium bromide (150 mg, 0.20 mmol, 1.00 equiv), TEA (102 mg, 1.01 mmol, 5.00 equiv). The resulting solution was stirred for 2 h at 120° C. in an oil bath. The reaction mixture was cooled to room temperature. The resulting solution was poured into 50 mL of water/ice. The resulting solution was extracted with 3×30 mL of ethyl acetate and the organic layers combined. The solvent was removed under reduced pressure. The residue was purified by preparative TLC (EtOAc:PE=20:1). This resulted in 30.8 mg (40%) of 6-chloro-2-(trifluoromethyl)-5-[4-(trifluoromethyl)phenoxy]-1H-indole as a white solid. (ES, m/z): 378 [M−H]⁻

H-NMR-PH-MRL-209-352-0: (300 MHz, DMSO, ppm): δ 12.63 (s, 1H), 7.69~7.73 (m, 4H), 7.02~7.08 (m, 3H).

Compound number 354 (i.e., 6-chloro-5-(pyridin-4-yl)-2-(trifluoromethyl)-1H-indole hydrochloride) was made as follows.

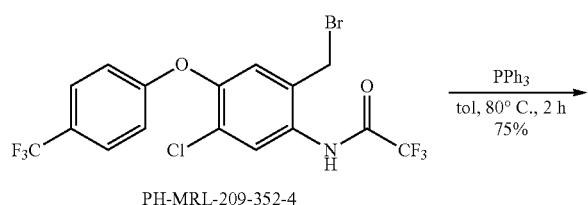

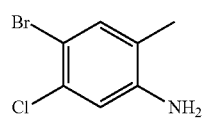

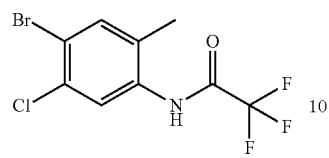

PH-MRL-209-353-1

First, a solution of 4-bromo-5-chloro-2-methylaniline (5 g, 22.68 mmol, 1.00 equiv), TFAA (5.5 g, 26.19 mmol, 1.50 equiv) in dichloromethane (50 mL) was placed into a 100-mL round-bottom flask. The resulting solution was stirred for 4 h at room temperature. The resulting mixture was concentrated under vacuum. This resulted in 7.9 g (crude) of N-(4-bromo-5-chloro-2-methylphenyl)-2,2,2-trifluoroacetamide as a brown solid.

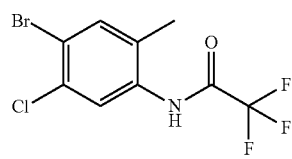

PH-MRL-209-353-1

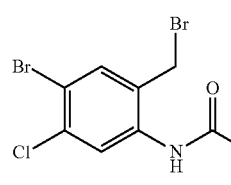

PH-MRL-209-353-2

Next, a solution of N-(4-bromo-5-chloro-2-methylphenyl)-2,2,2-trifluoroacetamide (7.9 g, 24.96 mmol, 1.00 equiv) in CCl₄ (100 mL), NBS (4.38 g, 24.61 mmol, 0.98 equiv) was placed into a 250-mL round-bottom flask. The resulting solution was stirred for 3 h at 60° C. The resulting mixture was concentrated under vacuum. The residue was applied onto a silica gel column with ethyl acetate/petroleum ether (1:10). This resulted in 10 g (crude) of N-[4-bromo-2-(bromomethyl)-5-chlorophenyl]-2,2,2-trifluoroacetamide as a brown solid.

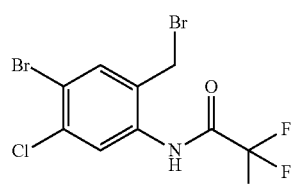

PH-MRL-209-353-2

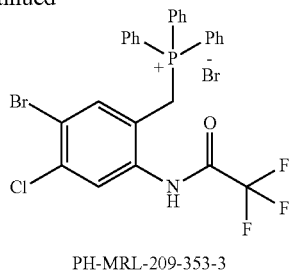

PH-MRL-209-353-3

Next, a solution of N-[4-bromo-2-(bromomethyl)-5-chlorophenyl]-2,2,2-trifluoroacetamide (11 g, 27.82 mmol, 1.00 equiv), PPh₃ (8.1 g, 30.88 mmol, 1.10 equiv) in Tol (100 mL) was placed into a 250-mL round-bottom flask. The resulting solution was stirred overnight at 100° C. The resulting mixture was concentrated under vacuum and washed by MeOH. This resulted in 9.2 g (50%) of [[5-bromo-4-chloro-2-(trifluoroacetamido)phenyl]methyl]triphenylphosphonium bromide as a yellow solid.

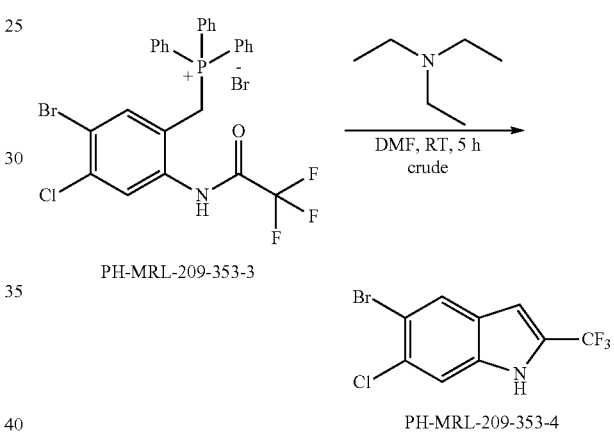

PH-MRL-209-353-3

PH-MRL-209-353-4

Next, a solution of [[5-bromo-4-chloro-2-(trifluoroacetamido)phenyl]methyl]triphenylphosphonium bromide (9.2 g, 13.99 mmol, 1.00 equiv), triethylamine (7.1 g, 70.17 mmol, 5.00 equiv) in N,N-dimethylformamide (120 mL) was placed into a 250-mL round-bottom flask. The resulting solution was stirred for 5 h at room temperature. The reaction was then quenched by the addition of 50 mL of water. The resulting solution was extracted with 3×100 mL of ethyl acetate and the organic layers combined and concentrated under vacuum. The residue was applied onto a silica gel column with ethyl acetate/petroleum ether (1:20). This resulted in 4.8 g (crude) of 5-bromo-6-chloro-2-(trifluoromethyl)-1H-indole as a yellow solid.

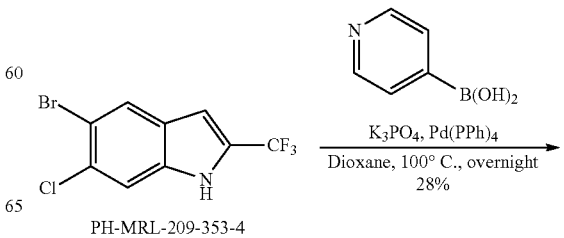

PH-MRL-209-353-4

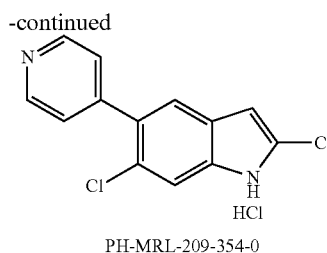

PH-MRL-209-354-0 HCl

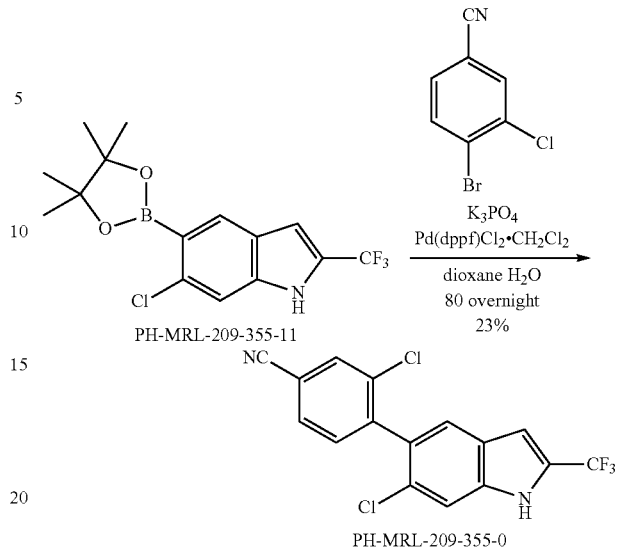

PH-MRL-209-355-11

PH-MRL-209-355-0

Finally, a solution of 5-bromo-6-chloro-2-(trifluoromethyl)-1H-indole (100 mg, 0.34 mmol, 1.00 equiv), $K_3PO_4$ (214.33 mg, 1.01 mmol, 3.00 equiv), Pd(PPh$_3$)$_4$ (39 mg, 0.03 mmol, 0.10 equiv), (pyridin-4-yl)boronic acid (82.23 mg, 0.67 mmol, 2.00 equiv) in dioxane/H$_2$O (6 mL/1 mL) was placed into a 50-mL round-bottom flask purged and maintained with an inert atmosphere of nitrogen. The resulting solution was stirred overnight at 100° C. The crude product was purified by Prep-HPLC. This resulted in 31 mg (28%) of 6-chloro-5-(pyridin-4-yl)-2-(trifluoromethyl)-1H-indole hydrochloride as a off-white solid. (ES, m/z): [M+H]$^+$ 333; $^1$H NMR (300 MHz, DMSO): 12.89-12.84 (m, 1H), 8.92 (d, J=6.6 Hz, 2H), 8.18-8.04 (m, 2H), 7.96 (d, J=4.2 Hz, 1H), 7.78 (d, J=3.3 Hz, 1H), 7.20 (s, 1H).

Compound number 355 (i.e., 3-chloro-4-[6-chloro-2-(trifluoromethyl)-1H-indol-5-yl]benzonitrile) was made as follows.

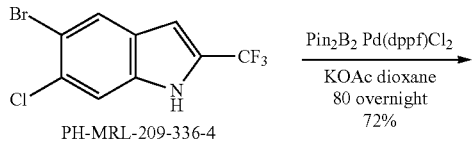

PH-MRL-209-336-4

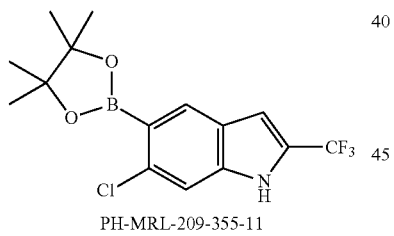

PH-MRL-209-355-11

Into a 100-mL round-bottom flask purged and maintained with an inert atmosphere of nitrogen, was placed dioxane (60 mL), 5-bromo-6-chloro-2-(trifluoromethyl)-1H-indole (3 g, 10.05 mmol, 1.00 equiv), Pin$_2$B$_2$ (5.1 g, 2.00 equiv), potassium acetate (2.95 g, 30.06 mmol, 3.00 equiv), Pd(dppf)Cl$_2$ (500 mg, 0.68 mmol, 0.07 equiv). The resulting solution was stirred overnight at 80° C. in an oil bath. The reaction mixture was cooled. The resulting solution was diluted with 50 mL of H$_2$O. The resulting solution was extracted with 3×50 mL of ethyl acetate and the organic layers combined. The resulting mixture was washed with 3×30 mL of brine. The organic phase was dried over anhydrous sodium sulfate and concentrated under vacuum. The residue was applied onto a silica gel column with ethyl acetate/petroleum ether (1:30-1:15). This resulted in 2.5 g (72%) of 6-chloro-5-(tetramethyl-1,3,2-dioxaborolan-2-yl)-2-(trifluoromethyl)-1H-indole as a white solid.

Next, into a 50-mL round-bottom flask purged and maintained with an inert atmosphere of nitrogen, was placed dioxane (5 mL), water (1 mL), 6-chloro-5-(tetramethyl-1,3,2-dioxaborolan-2-yl)-2-(trifluoromethyl)-1H-indole (100 mg, 0.29 mmol, 1.00 equiv), 4-bromo-3-chlorobenzonitrile (62.6 mg, 0.29 mmol, 1.00 equiv), (phosphoperoxy)potassium; dipotassium (184 mg, 0.866 mmol, 3.00 equiv), Pd(dppf)Cl$_2$.CH$_2$Cl$_2$ (21 mg, 0.10 equiv). The resulting solution was stirred overnight at 80° C. in an oil bath. The reaction mixture was cooled. The crude product was purified by Prep-HPLC product was obtained. This resulted in 23.9 mg (23%) of 3-chloro-4-[6-chloro-2-(trifluoromethyl)-1H-indol-5-yl]benzonitrile as a off-white solid. (ES, m/z): 353 [M−H]$^-$; (300 MHz, DMSO-d6, ppm): δ 12.64 (brs, 1H), 8.20 (s, 1H), 7.95-7.92 (m, 1H), 7.69 (s, 2H), 7.63-7.60 (d, J=8.1 Hz, 1H), 7.12 (s, 1H).

Compound number 356 (i.e., 6-chloro-5-(2-chloro-4-fluorophenyl)-2-(trifluoromethyl)-1H-indole) was made as follows.

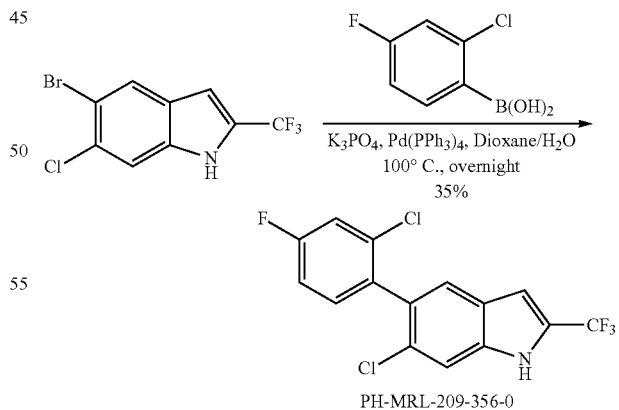

PH-MRL-209-356-0

Into a 40-mL round-bottom flask, was placed a solution of 5-bromo-6-chloro-2-(trifluoromethyl)-1H-indole (100 mg, 0.34 mmol, 1.00 equiv) in dioxane/H$_2$O (7 mL), (2-chloro-4-fluorophenyl)boronic acid (117.3 mg, 0.67 mmol, 2.00 equiv), K$_3$PO$_4$ (214 mg, 1.01 mmol, 3.00 equiv), Pd(PPh$_3$)$_4$ (39 mg, 0.03 mmol, 0.10 equiv). The resulting solution was stirred overnight at 100° C. The crude product was purified by Prep-HPLC. This resulted in 41 mg (35%) of 6-chloro-5-(2-chloro-4-fluorophenyl)-2-(trifluoromethyl)-1H-indole as brown oil. (ES, m/z): [M−H]⁻ 346; ¹H NMR (300 MHz, DMSO): 12.57 (brs, 1H), 7.65 (s, 2H), 7.60-7.56 (m, 1H), 7.46-7.41 (m, 1H), 7.35-7.28 (m, 1H), 7.09 (s, 1H).

Compound number 357 (i.e., 6-Chloro-5-(2,4-dichlorophenyl)-2-(trifluoromethyl)-1H-indole) was made as follows.

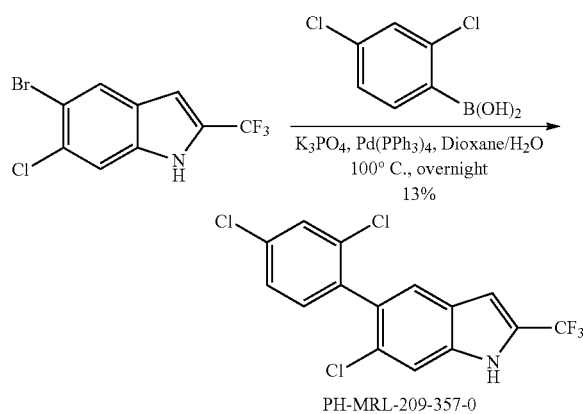

PH-MRL-209-357-0

Into a 50-mL round-bottom flask purged and maintained with an inert atmosphere of nitrogen, was placed a solution of 5-bromo-6-chloro-2-(trifluoromethyl)-1H-indole (100 mg, 0.34 mmol, 1.00 equiv) in Dioxane/H₂O (6 mL/1 mL), (2,4-dichlorophenyl)boronic acid (128 mg, 0.67 mmol, 2.00 equiv), K₃PO₄ (212 mg, 1.00 mmol, 3.00 equiv), Pd(PPh₃)₄ (39 mg, 0.03 mmol, 0.10 equiv). The resulting solution was stirred overnight at 100° C. The resulting mixture was concentrated under vacuum. The crude product was purified by Prep-HPLC. This resulted in 15.3 mg (13%) of 6-chloro-5-(2,4-dichlorophenyl)-2-(trifluoromethyl)-1H-indole as brown oil. (ES, m/z): [M−H]⁻ 362; ¹H NMR (300 MHz, DMSO): 12.59 (br s, 1H), 7.76 (d, J=2.1 Hz, 1H), 7.66 (s, 2H), 7.54-7.51 (m, 1H), 7.42 (d, J=8.4 Hz, 1H), 7.10 (s, 1H).

Compound number 358 (i.e., 2-[6-Chloro-2-(trifluoromethyl)-1H-indol-5-yl]benzoic acid) was made as follows.

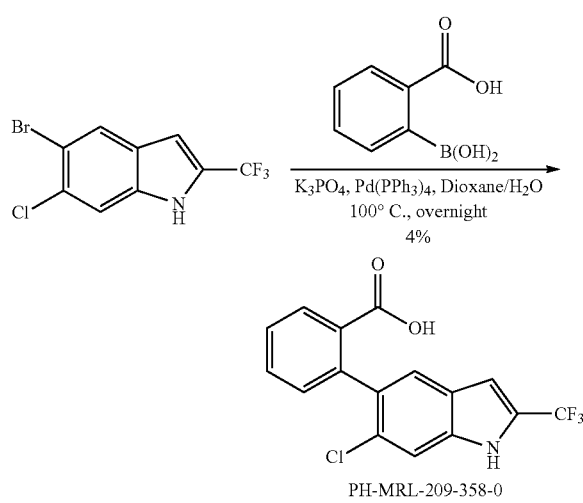

PH-MRL-209-358-0

Into a 50-mL round-bottom flask purged and maintained with an inert atmosphere of nitrogen, was placed a solution of 5-bromo-6-chloro-2-(trifluoromethyl)-1H-indole (200 mg, 0.67 mmol, 1.00 equiv) in Dioxane, H₂O (14 mL), 2-(dihydroxyboranyl)benzoic acid (223 mg, 1.34 mmol, 2.00 equiv), K₃PO₄ (427 mg, 2.01 mmol, 3.00 equiv), Pd(PPh₃)₄ (78 mg, 0.07 mmol, 0.10 equiv). The resulting solution was stirred overnight at 100° C. The crude product was purified by Prep-HPLC. This resulted in 10.2 mg (4%) of 2-[6-chloro-2-(trifluoromethyl)-1H-indol-5-yl]benzoic acid as a white solid. (ES, m/z): [M−H]⁻ 338; ¹H NMR (300 MHz, DMSO): 12.43 (br s, 1H), 7.96-7.91 (m, 1H), 7.65-7.60 (m, 1H), 7.56-7.49 (m, 3H), 7.31-7.29 (m, 1H), 7.06 (s, 1H).

Compound number 359 (i.e., 2-[6-Chloro-2-(trifluoromethyl)-1H-indol-5-yl]benzonitrile) was made as follows.

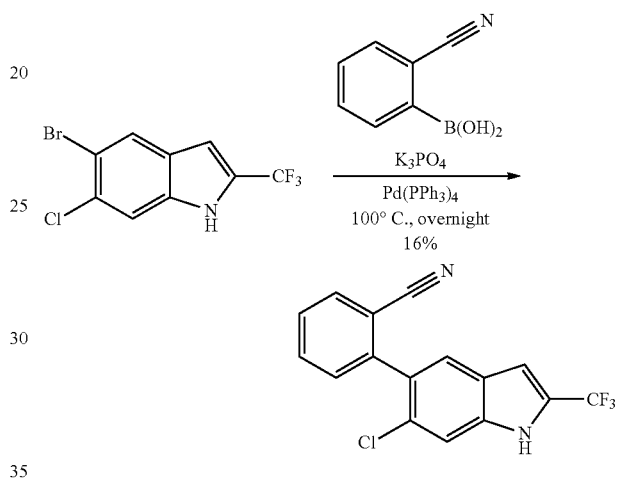

Into a 50-mL round-bottom flask purged and maintained with an inert atmosphere of nitrogen, was placed a solution of 5-bromo-6-chloro-2-(trifluoromethyl)-1H-indole (100 mg, 0.34 mmol, 1.00 equiv) in Dioxane, H₂O (7 mL), (2-cyanophenyl)boronic acid (99 mg, 0.67 mmol, 2.00 equiv), K₃PO₄ (214 mg, 1.01 mmol, 3.00 equiv), Pd(PPh₃)₄ (39 mg, 0.03 mmol, 0.10 equiv). The resulting solution was stirred overnight at 100° C. The resulting mixture was concentrated under vacuum. The crude product was purified by Prep-HPLC. This resulted in 17.4 mg (16%) of 2-[6-chloro-2-(trifluoromethyl)-1H-indol-5-yl]benzonitrile as a light yellow solid. (ES, m/z): [M−H]⁻ 319; ¹H NMR (300 MHz, DMSO): 12.66 (br s, 1H), 7.96 (d, J=8.1 Hz, 1H), 7.79 (d, J=7.8 Hz, 2H), 7.71 (s, 1H), 7.66 (d, J=7.5 Hz, 1H), 7.56 (d, J=8.1 Hz, 1H), 7.14 (s, 1H).

Compound number 360 (i.e., ([2-[6-Chloro-2-(trifluoromethyl)-1H-indol-5-yl]phenyl]methyl)dimethylamine) was made as follows.

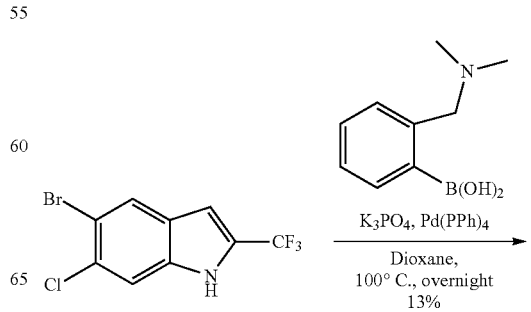

-continued

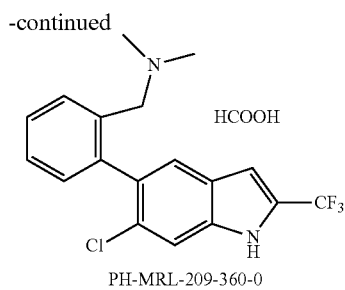

PH-MRL-209-360-0

Into a 50-mL round-bottom flask purged and maintained with an inert atmosphere of nitrogen, was placed a solution of 5-bromo-6-chloro-2-(trifluoromethyl)-1H-indole (100 mg, 0.34 mmol, 1.00 equiv) in Dioxane, H$_2$O (7 mL), 2-[(dimethylamino)methyl]phenylboronic acid (121 mg, 0.68 mmol, 2.00 equiv), K$_3$PO$_4$ (214 mg, 1.01 mmol, 3.00 equiv), Pd(PPh$_3$)$_4$ (39 mg, 0.03 mmol, 0.10 equiv). The resulting solution was stirred overnight at 100° C. The resulting mixture was concentrated under vacuum. The crude product was purified by Prep-HPLC. This resulted in 15.4 mg (13%) of ([2-[6-chloro-2-(trifluoromethyl)-1H-indol-5-yl]phenyl]methyl)dimethylamine as a white solid. (ES, m/z): [M+H]$^+$ 353; $^1$H NMR (300 MHz, DMSO): 12.63 (s, 1H), 9.66-9.59 (m, 1H), 7.80-7.69 (m, 3H), 7.60-7.51 (m, 2H), 7.33-7.30 (m, 2H), 7.10 (s, 1H), 4.34-4.28 (m, 1H), 3.95-3.90 (m, 1H), 2.73-2.64 (m, 3H), 2.51-2.46 (m, 3H).

Compound number 360-0A (i.e., ([2-[6-Chloro-2-(trifluoromethyl)-1H-indol-5-yl]phenyl]methyl)dimethylamine hydrochloride) was made as follows.

Into a 50-mL round-bottom flask, was placed a solution of 5-bromo-6-chloro-2-(trifluoromethyl)-1H-indole (100 mg, 0.34 mmol, 1.00 equiv) in Dioxane, H$_2$O (7 mL), 2-[(dimethylamino)methyl]phenylboronic acid (121 mg, 0.68 mmol, 2.00 equiv), K$_3$PO$_4$ (214 mg, 1.01 mmol, 3.00 equiv), Pd(PPh$_3$)$_4$ (39 mg, 0.03 mmol, 0.10 equiv). The resulting solution was stirred overnight at 100° C. The resulting mixture was concentrated under vacuum. The crude product was purified by Prep-HPLC. After that, conc HCl (aq, 1 mL) was added to the resulting solution and the solution was lyophilized. This resulted in 15.4 mg (12%) of ([2-[6-chloro-2-(trifluoromethyl)-1H-indol-5-yl]phenyl]methyl)dimethylamine hydrochloride as a yellow solid. (ES, m/z): [M+H]$^+$ 353; $^1$H NMR (300 MHz, DMSO): 12.77 (br s, 1H), 10.45 (br s, 1H), 7.96 (d, J=7.5 Hz, 1H), 7.81-7.70 (m, 2H), 7.58-7.52 (m, 2H), 7.39-7.24 (m, 1H). 7.19-7.10 (m, 1H), 4.31-4.21 (m, 1H), 3.94-3.88 (m, 1H), 2.62 (d, J=4.5 Hz, 3H), 2.46 (d, J=4.5 Hz, 3H).

Compound number 361 (i.e., 6-chloro-5-(3-chloropyridin-4-yl)-2-(trifluoromethyl)-1H-indole) was made as follows.

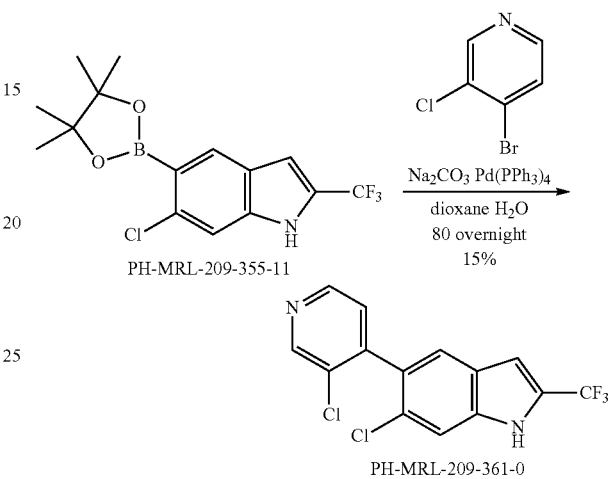

Into a 50-mL round-bottom flask purged and maintained with an inert atmosphere of nitrogen, was placed dioxane (10 mL), water (2 mL), 4-bromo-3-chloropyridine (111 mg, 0.58 mmol, 1.00 equiv), 6-chloro-5-(tetramethyl-1,3,2-dioxaborolan-2-yl)-2-(trifluoromethyl)-1H-indole (200 mg, 0.58 mmol, 1.00 equiv), sodium carbonate (122 mg, 1.14 mmol, 2.00 equiv), tetrakis(triphenylphosphine) palladium (66 mg, 0.06 mmol, 0.10 equiv). The resulting solution was stirred overnight at 80° C. in an oil bath. The reaction mixture was cooled. The crude product was purified by Prep-HPLC. This resulted in 28.4 mg (15%) of 6-chloro-5-(3-chloropyridin-4-yl)-2-(trifluoromethyl)-1H-indole as a white solid. (ES, m/z): 329 [M−H]$^−$; (300 MHz, DMSO-d6, ppm): δ 12.66 (brs, 1H), 8.77 (s, 1H), 8.63 (d, J=4.8 Hz, 1H), 7.72 (d, J=6.3 Hz, 2H), 7.49 (d, J=5.1 Hz, 1H), 7.13 (s, 1H).

Compound number 361-0A (i.e., 6-chloro-5-(3-chloropyridin-4-yl)-2-(trifluoromethyl)-1H-indole hydrochloride) was made as follows.

Into a 50-mL round-bottom flask purged and maintained with an inert atmosphere of nitrogen, was placed 6-chloro-5-(3-chloropyridin-4-yl)-2-(trifluoromethyl)-1H-indole (25 mg, 0.08 mmol, 1.00 equiv) and 10 ml water, 1 ml HCl. The combined aqueous layer was dried by lyophilization. This resulted in 25.2 mg (91%) of 6-chloro-5-(3-chloropyridin-4-yl)-2-(trifluoromethyl)-1H-indole hydrochloride as a white solid. (ES, m/z): 329 [M−HCl—H]$^-$; (300 MHz, DMSO-d6, ppm): δ 8.80 (s, 1H), 8.65 (d, J=5.1 Hz, 1H), 7.72 (d, J=3.6 Hz, 2H), 7.52 (d, J=4.8 Hz, 1H), 7.13 (s, 1H).

Compound number 362 (i.e., 6-chloro-5-(pyridin-4-yloxy)-2-(trifluoromethyl)-1H-indole; trifluoroacetic acid) was made as follows.

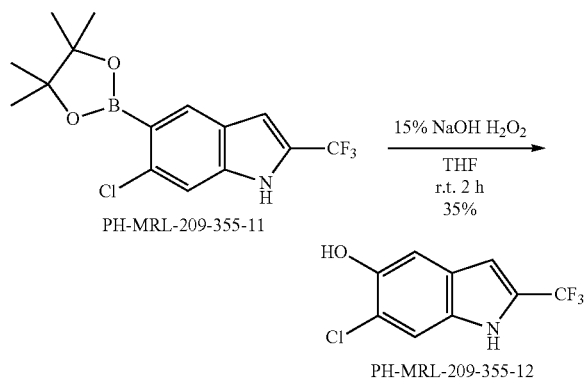

First, into a 100-mL 3-necked round-bottom flask was placed tetrahydrofuran (50 mL), 6-chloro-5-(tetramethyl-1,3,2-dioxaborolan-2-yl)-2-(trifluoromethyl)-1H-indole (2.5 g, 7.23 mmol, 1.00 equiv), then added 15% NaOH adjust the pH=9, the reaction mixture stirred for 10 min at r.t. then added hydrogen peroxide (8.2 g, 241.07 mmol, 10.00 equiv). The resulting solution was stirred for 2 h at room temperature. The resulting solution was diluted with 100 mL of ethyl acetate. The resulting mixture was washed with 3×30 mL of Brine. The mixture was dried over anhydrous sodium sulfate and concentrated under vacuum. The residue was applied onto a silica gel column with ethyl acetate/petroleum ether (1:30-1:20). This resulted in 600 mg (35%) of 6-chloro-2-(trifluoromethyl)-1H-indol-5-ol as a yellow solid.

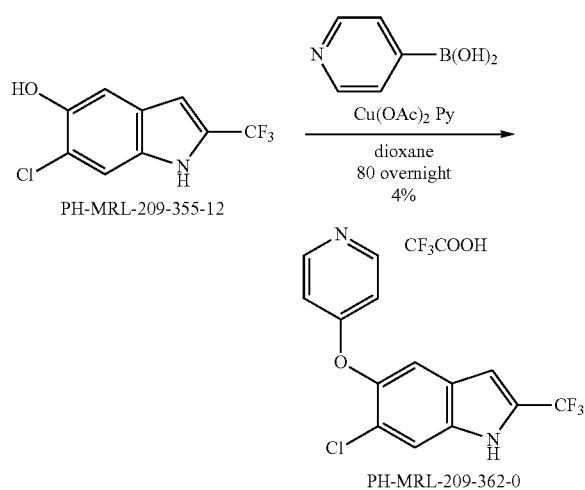

Next, into a 50-mL round-bottom flask purged and maintained with an inert atmosphere of nitrogen, was placed dioxane (10 mL), 6-chloro-2-(trifluoromethyl)-1H-indol-5-ol (230 mg, 0.98 mmol, 1.00 equiv), (pyridin-4-yl)boronic acid (180 mg, 1.46 mmol, 1.50 equiv), (acetyloxy)cuprio acetate (53 mg, 0.29 mmol, 0.30 equiv), pyridine (231 mg, 2.92 mmol, 3.00 equiv). The resulting solution was stirred overnight at 80° C. in an oil bath. The reaction mixture was cooled and the solid was filtered. The crude product was purified by Prep-HPLC product was obtained. This resulted in 15.8 mg (4%) of 6-chloro-5-(pyridin-4-yloxy)-2-(trifluoromethyl)-1H-indole; trifluoroacetic acid as a yellow solid. (ES, m/z): 313 [MS-CF$_3$COOH+H]$^+$; (300 MHz, DMSO-d6, ppm): δ 12.97 (s, 1H), 10.44 (s, 1H), 9.31 (d, J=5.4 Hz, 2H), 8.87 (t, J=7.8 Hz, 1H), 8.41 (t, J=7.8 Hz, 2H), 8.90 (s, 1H), 6.91 (s, 1H).

Compound number 362-0A (i.e., 6-chloro-5-(pyridin-4-yloxy)-2-(trifluoromethyl)-1H-indole hydrochloride) was made as follows.

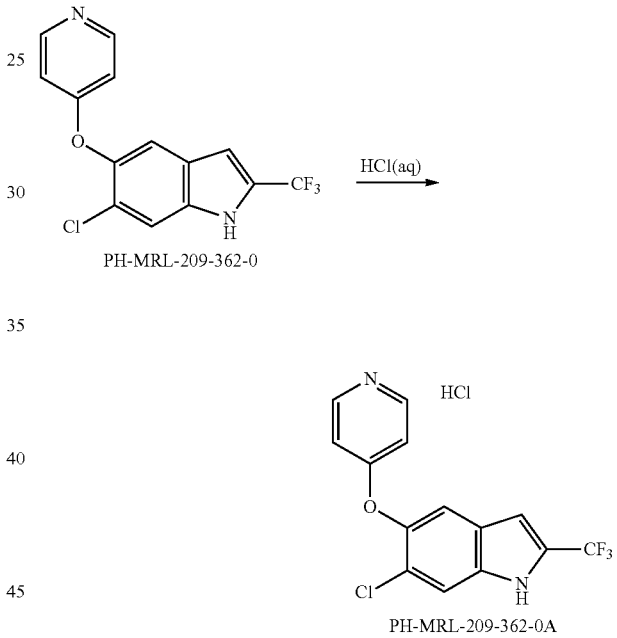

Into a 50-mL round-bottom flask, was placed 6-chloro-5-(pyridin-4-yloxy)-2-(trifluoromethyl)-1H-indole (15 mg, 0.05 mmol, 1.00 equiv), 10 ml water and 1 ml HCl. The combined aqueous layer was dried by lyophilization. This resulted in 16.7 mg of 6-chloro-5-(pyridin-4-yloxy)-2-(trifluoromethyl)-1H-indole hydrochloride as a grey solid. (ES, m/z): 313[Ms+H]$^+$; (300 MHz, DMSO-d6, ppm): δ 13.08 (s, 1H); 10.44 (s, 1H), 9.32 (d, J=2.4 Hz, 2H), 8.87 (t, J=8.7 Hz, 1H), 8.41-8.36 (m, 2H), 7.91 (s, 1H), 6.90 (s, 1H).

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:
1. A compound of formula:

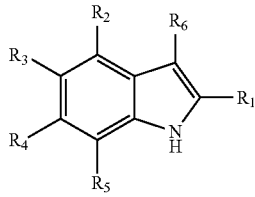

wherein:
R₁ is ($C_1$-$C_6$)-alkyl substituted with one or more halogens;
R₂ is H, halogen, ($C_1$-$C_6$)-alkyl or ($C_1$-$C_6$)-haloalkyl;
R₃ is biphenyl, naphthyl, aryl, aryl ether, or ($C_3$-$C_6$) cycloalkyl;
wherein the last three substituents may be unsubstituted or substituted with one or more of halogen, ($C_1$-$C_3$)-haloalkyl, ($C_1$-$C_3$)-haloalkoxy, aminoalkyl, cyano or carboxyl;
R₄ is halogen;
R₅ is H, halogen, ($C_1$-$C_6$)-alkyl or ($C_1$-$C_6$)-haloalkyl; and
R₆ is H, halogen, ($C_1$-$C_6$)-alkyl, ($C_2$-$C_5$)-alkenyl, or ($C_2$-$C_5$)-alkynyl, wherein each of ($C_1$-$C_6$)-alkyl, ($C_2$-$C_5$)-alkenyl, or ($C_2$-$C_5$)-alkynyl is independently unsubstituted or substituted with one or more halogens.

2. A compound according to claim 1 wherein R₁ is ($C_1$-$C_4$)-alkyl substituted with fluorine.
3. A compound according to claim 1 wherein R₂ is Cl.
4. A compound according to claim 1 wherein R₃ is a mono- or bi-halogen substituted phenyl ether.
5. A compound according to claim 1 wherein R₃ is a bi- or tri-halogen substituted phenyl.
6. A compound according to claim 4 wherein the halogen is chlorine, bromine or fluorine.
7. A compound according to claim 5 wherein the halogen is chlorine, bromine or fluorine.
8. A compound according to claim 1 wherein R₄ is chlorine.
9. A compound according to claim 1 wherein R₅ is hydrogen.
10. A composition for treating helminth infestation comprising an anthelmintically effective amount of the compound of claim 1 and a pharmaceutically acceptable carrier.
11. A composition for treating helminth infestation according to claim 10 wherein the compound of formula (I) is combined with an additional active agent selected from the group consisting of acaricides, anthelmintics, anti-parasitics and insecticides.
12. A composition for treating helminth infestation according to claim 11 wherein the active agent is a macrocyclic lactone.
13. A composition for treating helminth infestation according to claim 12 wherein the macrocyclic lactone is selected from the group consisting of abamectin, dimadectin, doramectin, emamectin, eprinomectin, ivermectin, latidectin, lepimectin, selamectin or ML-1,694,554.
14. A composition for treating helminth infestation according to claim 10 wherein the compound of formula (I) is combined with verapamil.
15. A method for treating helminth infestation comprising administration of an anthelmintically effective amount of the compound of claim 1 to an animal in need thereof.
16. A method according to claim 15 in which the helminths are trematodes.
17. A method according to claim 16 in which the helminths are *Fasciola hepatica*.
18. A compound of formula:

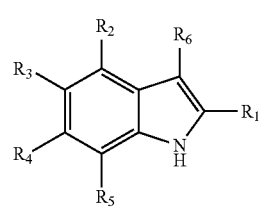

wherein:
R₁ is CF₃;
R₂ is H;
R₃ is phenyl or heteroaryl;
wherein the phenyl or heteroaryl is unsubstituted or substituted with one or more of halogen, ($C_1$-$C_3$)-haloalkyl or cyano;
R₄ is halogen;
R₅ is H; and
R₆ is H.

19. A compound according to claim 18 wherein the heteroaryl is a pyridine.
20. A composition for treating helminth infestation comprising an anthelmintically effective amount of the compound of claim 18 and a pharmaceutically acceptable carrier.
21. A composition for treating helminth infestation according to claim 20 wherein the compound of formula (I) is combined with an additional active agent selected from the group consisting of acaricides, anthelmintics, anti-parasitics and insecticides.
22. A composition for treating helminth infestation according to claim 21 wherein the active agent is a macrocyclic lactone.
23. A composition for treating helminth infestation according to claim 22 wherein the macrocyclic lactone is selected from the group consisting of abamectin, dimadectin, doramectin, emamectin, eprinomectin, ivermectin, latidectin, lepimectin, selamectin or ML-1,694,554.
24. A composition for treating helminth infestation according to claim 20 wherein the compound of formula (I) is combined with verapamil.
25. A method for treating helminth infestation comprising administration of an anthelmintically effective amount of the compound of claim 18 to an animal in need thereof.
26. A method according to claim 25 in which the helminths are trematodes.
27. A method according to claim 26 in which the helminths are *Fasciola hepatica*.

* * * * *